US010994032B2

(12) United States Patent
Kjaer et al.

(10) Patent No.: US 10,994,032 B2
(45) Date of Patent: May 4, 2021

(54) 177-LU LABELED PEPTIDE FOR SITE-SPECIFIC UPAR-TARGETING

(71) Applicant: TRT Innovations APS, Copenhagen (DK)

(72) Inventors: Andreas Kjaer, Frederiksberg (DK); Morten Persson, Copenhagen (DK); Michael Ploug, Copenhagen (DK)

(73) Assignee: TRT Innovations APS, Copenhagen (DK)

( * ) Notice: Subject to any disclaimer, the term of this patent is extended or adjusted under 35 U.S.C. 154(b) by 5 days.

(21) Appl. No.: 14/399,820

(22) PCT Filed: May 3, 2013

(86) PCT No.: PCT/DK2013/050126
§ 371 (c)(1),
(2) Date: Nov. 7, 2014

(87) PCT Pub. No.: WO2013/167130
PCT Pub. Date: Nov. 14, 2013

(65) Prior Publication Data
US 2015/0132219 A1 May 14, 2015

Related U.S. Application Data

(60) Provisional application No. 61/644,059, filed on May 8, 2012.

(30) Foreign Application Priority Data

May 8, 2012 (DK) .......................... PA 2012 00321

(51) Int. Cl.
*A61K 51/08* (2006.01)
*C12N 9/72* (2006.01)
*C07K 16/28* (2006.01)

(52) U.S. Cl.
CPC ........ *A61K 51/088* (2013.01); *C07K 16/2896* (2013.01); *C12N 9/6456* (2013.01)

(58) Field of Classification Search
CPC ...... A61K 51/00; A61K 51/08; A61K 51/088; A61K 2121/00; A61K 2123/00; C07K 16/2896; C12N 9/6456; A61P 35/00
USPC ...... 424/1.11, 1.65, 1.69, 1.73, 9.1, 9.2, 9.6; 514/1, 1.1, 19.2, 19.3, 19.4, 19.5, 19.6, 514/21.1, 21.5, 21.6, 21.7; 530/300, 317, 530/324, 325, 326, 327, 328; 534/7, 15
See application file for complete search history.

(56) References Cited

U.S. PATENT DOCUMENTS

| | | |
|---|---|---|
| 4,444,690 A | 4/1984 | Fritzberg |
| 4,479,930 A | 10/1984 | Hnatowich |
| 4,861,869 A | 8/1989 | Nicolotti et al. |
| 4,965,392 A | 10/1990 | Fritzberg et al. |
| 5,120,526 A | 6/1992 | Fritzberg et al. |
| 5,175,257 A | 12/1992 | Ksina et al. |
| 5,310,536 A | 5/1994 | Srinivasan |
| 5,830,431 A | 11/1998 | Srinivasan et al. |
| 6,277,818 B1 | 8/2001 | Mazar et al. |
| 6,514,710 B1 | 2/2003 | Jones et al. |
| 7,026,282 B1 | 4/2006 | Ploug et al. |
| 8,568,689 B1* | 10/2013 | Cuthbertson ........ A61K 51/088 424/1.11 |
| 9,884,131 B2* | 2/2018 | Kjaer ..................... A61K 38/08 |
| 10,111,969 B2* | 10/2018 | Kjaer ................. A61K 49/0032 |
| 2007/0190068 A1* | 8/2007 | Hart .................... A61K 47/6849 424/179.1 |

FOREIGN PATENT DOCUMENTS

| | | | |
|---|---|---|---|
| WO | WO 01/25410 A2 | 4/2001 | |
| WO | WO 2006/036071 A2 | 4/2006 | |
| WO | WO-2006036071 A2 * | 4/2006 | .......... A61K 51/088 |
| WO | WO 2007/134274 A2 | 11/2007 | |

OTHER PUBLICATIONS

Li et al (Clin. Cancer Res., 2008, vol. 14, pp. 4758-4766).*
Volkert et al, J. Nucl. Med., 1991, vol. 32, pp. 174-185.*
Persson et al, Nuclear Medicine and Biology, Published online on Dec. 14, 2011, No. 39, pp. 560-569.*
Knor et al (Eur. J. Nucl. Med. Mol. Imaging, 2008, vol. 35, pp. 53-64).*
Knor et al, European Journal of Nuclear Medicine and Molecular Imaging, 2008, vol. 35, No. 1, pp. 53-64.*
Ploug et al, Biochemistry, 2001, vol. 40, No1. 12157-12168.*
Persson et al, J. Nucl. Med., Jan. 2012, vol. 53, pp. 138-145.*
Volkert et al, Journal of Nuclear Medicine, vol. 32, No. 1, Jan. 1991, pp. 174-185. (Year: 1991).*
Li et al, Clinical Cancer Research, vol. 14, No. 15, pp. 4758-4766 (Year: 2008).*
Persson et al.: "Quantitative PET of Human Urokinase-Type Plasminogen Activator Receptor with $^{64}$Cu-DOTA-AE105: Implications for Visualizing Cancer Invasion", The Journal of Nuclear Medicine, vol. 53, No. 1, Jan. 2012, pp. 138-145.
Ploug et al.: "Peptide-Derived Antagonists of the Urokinase Receptor. Affinity Maturation by Combinatorial Chemistry, Identification of Functional Epitopes, and Inhibitory Effect on Cancer Cell Intravasation", Biochemistry, Vo. 40, No. 40, 2001, pp. 12157-12168.
Ekaterina Dadachova: "Cancer Therapy with Alpha-Emitters Labeled Peptides", Seminars in Nuclear Medicine, vol. 40, No. 3, May 2010, pp. 204-208.
Guha et al.: "Tumor Biology-Guided Radiotherapy Treatment Planning: Gross Tumor Volume Versus Functional Tumor Volume", Seminars in Nuclear Medicine, vol. 38, No. 2, Mar. 2008, pp. 105-113.

(Continued)

*Primary Examiner* — D. L. Jones
(74) *Attorney, Agent, or Firm* — Merchant & Gould P.C.

(57) ABSTRACT

There is provided a 177-Lu labelled peptide for site-specific targeting of the Urokinase Plasminogen Activator Receptor (uPAR) thereby enabling treatment of a cancer disease associated with high uPAR expression; e.g. treatment of colorectal cancer by administering to a patient an effective amount of the 177-Lu labelled peptide.

6 Claims, 12 Drawing Sheets

(56) References Cited

OTHER PUBLICATIONS

Jiang et al.: "Preliminary evaluation of $^{177}$Lu-labeled knottin peptides for integrin receptor-targeted radionuclide therapy", European Journal of Nuclear Medicine and Molecular Imaging, vol. 38, No. 4, Apr. 2011 pp. 613-622.
Knör et al.: "Development and evaluation of peptidic ligands targeting tumour-associated urokinase plasminogen activator receptor (uPAR) for use in α-emitter therapy for disseminated ovarian cancer", European Journal of Nuclear Medicine and Molecular Imaging, vol. 35, No. 1, 2008, pp. 53-64.
Lewis et al.: "Biological comparison of $^{149}$Pm-, $^{166}$Ho-, and $^{177}$Lu-DOTA-biotin pretargeted by CC49 scFv-streptavidin fusion protein in xenograftbearing nude mice", Nuclear Medicine and Biology, Vo. 31, No. 7, Oct. 2004, pp. 213-223.
Li et al.: "$^{68}$Imaging of Urokinase-Type Plasminogen Activator Receptor Expression Using a 64Cu-Labeled Linear Peptide Antagonist by microPET", Clinical Cancer Research, vol. 14, No. 15, Aug. 1, 2008, pp. 4758-4766.
Persson et al.: "$^{68}$Ga-labeling and in vivo evaluation of a uPAR binding DOTA- and NODAGA-conjugated peptide for PET imaging of invasive cancers", Nuclear Medicine and Biology, vol. 39, No. 4, May 2012, pp. 560-569.
Persson et al.: "New peptide receptor radionuclide therapy of invasive cancer cells in vivo studies using $^{177}$Lu-DOTA-AE105 targeting uPAR in human colorectal cancer xenografts", Nuclear Medicine and Biology, vol. 39, No. 7, Oct. 2012, pp. 962-969.
International Search Report dated Jul. 5, 2013 for International Patent Application No. PCT/DK2013/050126, filed May 3, 2013.
Written Opinion of the International Searching Authority dated Jul. 5, 2013 for International Patent Application No. PCT/DK2013/050126, filed May 3, 2013.
International Preliminary Report on Patentability dated Nov. 11, 2014 for International Patent Application No. PCT/DK2013/050126, filed May 3, 2013.
Wild D, Frischknecht M, Zhang H, Morgenstern A, Bruchertseifer F, Boisclair J, Provencher-Bolliger A, Reubi JC, Maecke HR. Alpha- versus beta-particle radiopeptide therapy in a human prostate cancer model (213Bi-DOTA-PESIN and 213Bi-AMBA versus 177Lu-DOTA-PESIN). *Cancer Res.* Feb. 1, 2011;71(3):1009-18.
Kratochwil C, Giesel FL, Bruchertseifer F, Mier W, Apostolidis C, Boll R, Murphy K, Haberkorn U, Morgenstern A. $^{213}$Bi-DOTATOC Receptor-targeted alpha-radionuclide therapy induces remission in neuroendocrine tumours refractory to beta radiation: a first-in-human experience. *Eur J Nucl Med Mol Imaging.* Nov. 2014;41(11):2106-19.
De Bock, Wnag Y. Clincal significance of urokinase-type plasminogen activator receptor (uPAR) expression in cancer. *Med Res Rev*, 24, No. 1, 13-39, 2004.
Brady D, O'Sullivan JM, Prise KM . . . What is the role of the bystander response in radionuclide therapies? *Front Oncol* (2013) 3:215.10.3389/fonc.2013.00215.
Prise KM, Schettino G, Folkard M, Held KD . . . New insights on cell death from radiation exposure. *Lancet Oncol* (2005) 6(7):520.
Boyd M, Ross SC, Dorrens J, Fullerton NE, Tan KW, Zalutsky MR, et al. Radiation-induced biologic bystander effect elicited in vitro by targeted radiopharmaceuticals labeled with alpha-, beta-, and auger electron-emitting radionuclides. *J Nucl Med* (2006) 47(6):1007-15.
Koppe et al., Biodistribution and Therapeutic Efficacy of 125/131I-, 186Re-, 88/90Y-, or 177Lu-Labeled Monoclonal Antibody MN-14 to Carcinoembryonic Antigen in Mice with Small Peritoneal Metastases of Colorectal Origin, The Journal of Nuclear Medicine, vol. 45, No. 7 (2007).
Jean Claude Reubi et al., "Affinity profiles for human somatostatin receptor subtypes SST1-SST5 of somatostatin radiotracers selected for scintigraphic and radiotherapeutic use", European Journal of Nuclear Medicine, vol. 21., No. 3, Mar. 2000.
Hicks et al., "64Cu-SARTATE PET Imaging of Patients with Neuroendocrine Tumors Demonstrates High Tumor Uptake and Retention, Potentially Allowing Prospective Dosimetry for Peptide Receptor Radionuclide Therapy", J Nucl Med., 60:777-785 (2019).
Talip et al., "A Step-by-Step Guide for the Novel Radiometal Production for Medical Applications: Case Studies with 68Ga, 44Sc, 177Lu and 161Tb", Molecules, 25(4), 966 (2020).
Lakes et al., Evaluating 225Ac and 177Lu Radioimmunoconjugates against Antibody-Drug Conjugates for Small-Cell Lung Cancer, Molecular pharmaceutics, 4270-4279, (2020).

\* cited by examiner

A)

uPAR Theranostics

PET Imaging / Diagnostics          Targeted Radionuclide Therapy

B)

Treatment groups (n=12 mice/group)

Gr. 1: Vehicle (6 mice inoculated day 14 + 6 mice inoculated 1 day before first dose)

Gr. 2: $^{177}$Lu-DOTA-AE105Mut (Control)

Gr. 3: $^{177}$Lu-DOTA-AE105

US 10,994,032 B2

177-LU LABELED PEPTIDE FOR SITE-SPECIFIC UPAR-TARGETING

This application is a National Stage Application of PCT/DK2013/050126, filed 3 May 2013, which claims benefit of Serial No. PA 2012 00321, filed 8 May 2012 in Denmark, and which claims benefit of U.S. Provisional Ser. No. 61/644,059, filed 8 May 2012, and which applications are incorporated herein by reference. To the extent appropriate, a claim of priority is made to each of the above disclosed applications.

FIELD OF THE INVENTION

The present invention relates to a 177-Lu labelled peptide for site-specific targeting of the Urokinase Plasminogen Activator Receptor (uPAR). More specifically the invention relates to the treatment of any cancer disease associated with high uPAR expression. In particular the present invention is directed to but not limited to the treatment of prostate, breast and colorectal cancer by administering to a patient an effective amount of the 177-Lu labelled peptide.

BACKGROUND OF THE INVENTION

Various radio-labelled peptide compositions have been developed or are under development for site-specific targeting of a therapeutic radionuclide. The general principle involves attaching a selected radionuclide to a peptide having a high specificity for a particular organ or tissue so that the organ or tissue can be treated by a therapeutic radioisotope. This field of research has shown particular applicability for tumor imaging and treatment. Particularly desirable biological sites include but is not limited to neuroendocrine tumors, such as abdominal tumors, and small cell lung carcinomas, brain tumors, prostate tumors, breast tumors, colon tumors, and ovarian tumors.

DOTA (1,4,7,10-tetrakis(carboxymethyl)-1,4,7,10 tetraazacyclo dodecane) and its derivatives constitute an important class of chelators for biomedical applications as they accommodate very stably a variety of di- and trivalent metal ions. An emerging area is the use of chelator conjugated bioactive peptides for labelling with radiometals in different fields of diagnostic and therapeutic nuclear oncology. NODAGA and its derivatives constitute another important class of chelators for biomedical applications.

$^{177}$Lu-labeled peptides for nuclide targeting therapy are successfully being introduced in treatment of neuroendocrine tumors and several new targets are currently being evaluated in pre-clinical cancer models including integrins, Her-2, Gastrin-releasing peptide (GRP), and vascular endothelial growth factor (VEGF).

uPAR PET imaging has been exploited in several human cancer xenograft models using a small linear DOTA-conjugated peptide, DOTA-AE105 radiolabeled with $^{64}$Cu (Persson et al, 2011) and $^{68}$Ga (Persson et al, 2012)

Malignant tumors are capable of degrading the surrounding extracellular matrix, resulting in local invasion or metastasis. Urokinase-type plasminogen activator (uPA) and its cell surface receptor (uPAR) are central molecules for cell surface-associated plasminogen activation both in vitro and in vivo. High expression of uPA and uPAR in many types of human cancers correlate with malignant tumor growth and associate with a poor prognosis, possibly indicating a causal role for the uPA/uPAR system in cancer progression and metastasis. Studies by immunohistochemistry and in situ hybridization indicate that expression levels of the components from the uPA system are generally very low in normal tissues and benign lesions. It has also been reported that the uPA/uPAR system is involved in regulating cell-extracellular matrix interactions by acting as an adhesion receptor for vitronectin and by modulating integrin function. Based on these properties, the uPA/uPAR system is consequently considered an attractive target for cancer therapy.

WO 01/25410 describes diagnostically or therapeutically labelled uPAR-targeting proteins and peptides. The peptide or protein comprises at least 38 amino acid residues, including residues 13-30 of the uPAR binding site of uPA.

U.S. Pat. No. 6,277,818 describes uPAR-targeting cyclic peptide compounds that may be conjugated with a diagnostic label. The peptides are based on the amino acid residues 20-30 of uPA.

U.S. Pat. No. 6,514,710 is also directed to cyclic peptides having affinity for uPAR. The peptides may carry a detectable label. The peptide comprises 11 amino acids joined by a linking unit.

Ploug et al. in Biochemistry 2001, 40, 12457-12168 describes uPAR targeting peptides but not in the context of imaging, including amino acid sequences as described in the present document. Similar disclosure is provided in U.S. Pat. No. 7,026,282.

DADACHOVA, E. ("Cancer Therapy with Alpha-Emitters Labeled Peptides", Seminars In Nuclear Medicine (2010), Vol. 40, Issue 3, Pages 204-208) discloses 213-Bi labelled uPAR binding peptide conjugates, in which the peptide is coupled to 213-Bi by DOTA. The petides are used for treatment of cancer.

GUHA, A. C. et al. ("Tumor Biology-Guided Radiotherapy Treatment Planning: Gross Tumor Volume Versus Functional Tumor Volume", Seminars In Nuclear Medicine (2008), Vol. 38, Issue 2, Pages 105-113) discloses that radioactive metals, such as 177-Lu, are used for labelling antibodies for use in radio immunotherapy. The document further describes that the radioactive metals may be conjugated to functional binding agents, such as uPAR binding peptides, by metal chelating agents.

JIANG L. et al.("Preliminary evaluation of (177)Lu-labeled knottin peptides for integrin receptor-targeted radionuclide therapy", Eur. J. Nucl. Med. Mol. Imaging (2011), Vol. 38, Issue 4, pages 13-22) discloses cysteine knot peptides engineered to bind integrin receptors, which are radio labelled with 177-Lu via the radio metal chelator DOTA, and the use of such peptide for radiotherapy of integrin positive tumors.

WO2007134274 A2 discloses a method for killing cancer stem cells by use of a ligand that binds to uPAR conjugated to 177-Lu.

Selecting a specific radionuclide in a specific conjugate system is not trivial due to chemical and physiological uncertainties. For instance it would not be obvious to replace 213-Bi with 177-Lu, since 213-Bi is an alpha-emitter and thus clinically remote from 177-Lu, which is a beta-emitter.

The efficient targeting of uPAR demands a selective high-affinity vector that is chemically robust and stable.

SUMMARY OF THE INVENTION

The present invention provides 177-Lu labelled peptides having high affinity for uPAR, high potency in a cell-binding system, and demonstrated biological stability. More specifically the invention relates to the treatment of a cancer disease associated with high uPAR expression. In particular the present invention is directed to but not limited to the treatment of prostate, breast and colorectal cancer by administering to a patient an effective amount of the 177-Lu labelled peptide.

In a first aspect the present invention relates to a 177-Lu labelled uPAR binding peptide conjugate, wherein the peptide is coupled to 177-Lu by a chelating agent.

In a preferred embodiment the present invention relates to a 177-Lu labelled peptide conjugate, wherein the peptide is coupled to 177-Lu by a chelating agent, said peptide is selected from the group consisting of:

(D-Asp)-([beta]-cyclohexyl-L-alanine)-(Phe)-(D-Ser)-(D-Arg)-(Tyr)-(Leu)-(Trp)-(Ser), (Ser)-(Leu)-([beta]-cyclohexyl-L-alanine)-(Phe)-(D-Ser)-(Gln)-(Tyr)(Leu)-(Trp)-(Ser), (D-Glu)-([beta]-cyclohexyl-L-alanine)-(Phe)-(D-Ser)-(D-Tyr)-(Tyr)-(Leu)-(Trp)-(Ser), (Asp)-([beta]-cyclohexyl-L-alanine)-(Phe)-(D-Ser)-(D-Arg)-(Tyr)-(Leu)-(Trp)-(Ser), (Asp)-([beta]-cyclohexyl-L-alanine)-(Phe)-(Ser)-(D-Arg)-(Tyr)-Leu)-(Trp)-(Ser), (D-Asp)-([beta]-cyclohexyl-L-alanine)-(Phe)-(Ser)-(D-Arg)-(Tyr)-Leu)-(Trp)-(Ser), (D-Thr)-([beta]-cyclohexyl-L-alanine)-(Phe)-(D-Ser)-(D-Arg)-(Tyr)-(Leu)-(Trp)-(Ser), (D-Asp)-([beta]-cyclohexyl-L-alanine)-(Phe)-(D-Ser)-(D-Arg)-(Tyr)-(Leu)-([beta]-2-naphthyl-L-alanine)-(Ser), (Asp)-([beta]-cyclohexyl-L-alanine)-(Phe)-(D-Ser)-(Arg)-(Tyr)-(Leu)-(Trp)-(Ser), (Asp)-([beta]-cyclohexyl-L-alanine)-(Phe)-(D-Ser)-(D-Arg)-(Tyr)-(Leu)([beta]-1-naphthyl-L-alanine)-(Ser), (D-Glu)-([beta]-cyclohexyl-L-alanine)-(Phe)-(D-Ser)-(Tyr)-(Tyr)-(Leu)-(Trp)-(Ser), (Asp)-([beta]-cyclohexyl-L-alanine)-(Phe)-(D-Ser)-(D-Arg)-(Leu)-(Leu)-(Trp)-(D-His), (Asp)-([beta]-cyclohexyl-L-alanine)-(Phe)-(D-Ser)-(D-Arg)-([beta]-cyclohexyl-L-alanine)-(Leu)-(Trp)-(Ile), (Asp)-([beta]-cyclohexyl-L-alanine)-(Phe)-(D-Ser)-(D-Arg)-(Tyr)-(Leu)([beta]-1-naphthyl-L-alanine)-(D-His), (Asp)-([beta]-cyclohexyl-L-alanine)-(Phe)-(D-Ser)-(D-Arg)-(N-(2,3-dimethoxybenzyl)glycine)-(D-Phe)-(N-(3-indolylethyl)glycine)-(N-(2-methoxyethyl)glycine), (Asp)-([beta]-cyclohexyl-L-alanine)-(Phe)-(D-Ser)-(D-Arg)-(N-(2,3-dimethoxybenzyl)glycine)-(D-Phe)-(N-benzylglycine)-(N-(2[beta]thoxyethyl)glycine), (Asp)-([beta]-cyclohexyl-L-alanine)-(Phe)-(D-Ser)-(D-Arg)-(N-(2,3-dimethoxybenzyl)glycine)-(D-Phe)-(N-(methylnaphthalyl)glycine)-(N-(2-methoxyethyl)glycine), and (Asp)-([beta]-cyclohexyl-L-alanine)-(Phe)-(D-Ser)-(D-Arg)-(N-(2,3-dimethoxybenzyl)glycine)-(D-Phe)-(N-(2,3-dimethoxybenzyl)glycine)-(Ile).

Preferably the chelating agent is DOTA, NOTA, NODAGA or CB-TE2A and preferably the peptide is (D-Asp)-([beta]-cyclohexyl-L-alanine)-(Phe)-(D-Ser)-(D-Arg)-(Tyr)-(Leu)-(Trp)-(Ser).

Particularly preferred is the 177-Lu labelled peptide conjugate with the formula:

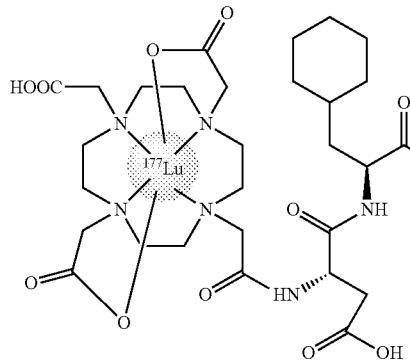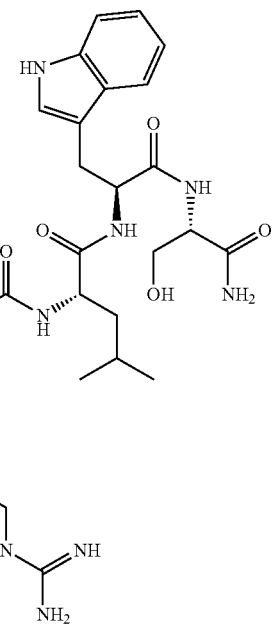

In further aspects the present invention relates to the 177-Lu labelled peptides defined above for use as a medicament, to the use of the 177-Lu labelled peptides above for the manufacture of a medicament for treatment of cancer, especially but not limited to prostate, breast and colorectal cancer, and to a pharmaceutical composition comprising the 177-Lu labelled peptides of the invention. Similar methods of treatment are encompassed by the present invention.

The present inventors have surprisingly found that the 177-Lu labelled peptides of the present invention are stable in vivo and capable of inducing cytotoxic effects in tumors but not in the surrounding tissue. Hence, the 177-Lu labelled peptides of the present invention constitute the optimal radionuclide for therapy of small tumor lesions and/or disseminated metastatic disease. The 177-Lu labelled peptides of the present invention specifically target uPAR-positive cancer cells, and in particular the most aggressive (metastatic) cells, in a human colorectal cancer model.

Moreover, the peptides of the present invention can be used for non-invasive detection and quantification of the expression level of uPAR using PET imaging. Using 177-labeled peptide also SPECT imaging is possible. Accordingly, systemic radiotherapy with the 177-Lu labelled peptides of the present invention are useful as a new treatment in cancer patients, which have confirmed high levels of uPAR expression identified using uPAR PET imaging.

DETAILED DESCRIPTION OF THE INVENTION

Figure 1:
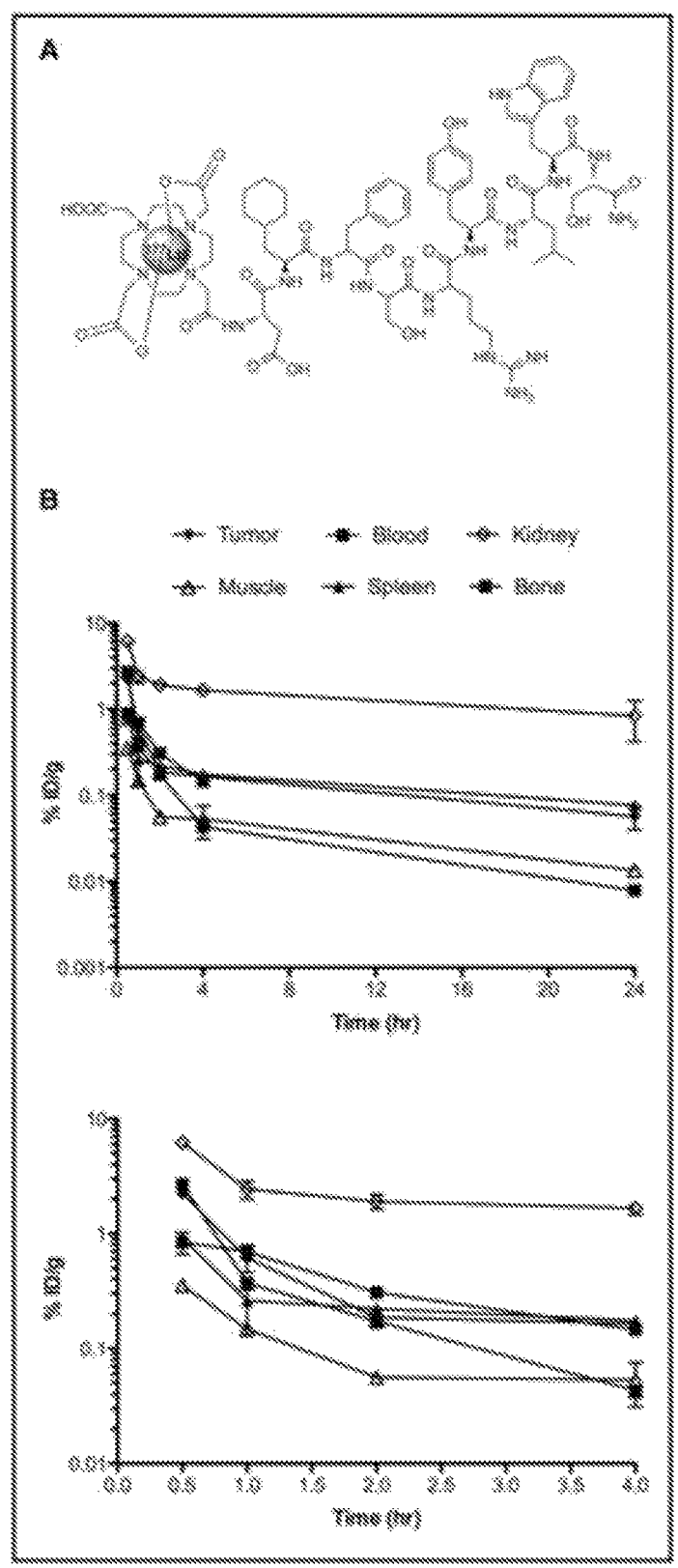
FIG. 1 shows the chemical structure and biodistribution of $^{177}$Lu-DOTA-AE105 in selected organs and primary tumor lesions in HT-29 tumor xenograft bearing Nude mice.

Surprisingly, a radiolabeled peptide of the present invention having an unmodified carboxy terminal amino acid exhibits improved in vivo properties when compared to corresponding radiolabeled peptides that have been specifically modified to remove the carboxylic acid at the carboxy terminal amino acid. In particular, the radiolabeled peptides of this invention display improved blood and liver clearance as well as improved biological site uptake and retention time.

The peptide selected for use in the radiopharmaceutical of the present invention is radiolabeled by coupling a chelating agent to the peptide. The chelating agent is capable of binding a selected radionuclide thereto. The chelating agent and radionuclide are coupled to the peptide in a manner that does not interfere or adversely affect the binding properties or specificity of the peptide. The use of various chelating agents for radio labeling peptides is well known in the art. Suitable chelating agents generally include those which contain a tetradentate ligand with at least one sulfur group available for binding the metal radionuclide such as the known $N_3S$ and $N_2S_2$ ligands. More particularly, chelating groups that may be used in conjunction with the peptides of the present invention include 2,3-bis(mercaptoacetamido) propanoate (U.S. Pat. No. 4,444,690), S-benzoylmercaptoacetylglycylglycylglycine (U.S. Pat. No. 4,861,869), dicyclic dianhydrides such as DTPA and EDTA and derivatives thereof (U.S. Pat. No. 4,479,930), NS chelates containing amino groups to enhance chelation kinetics (U.S. Pat. No. 5,310,536), $N_2S_2$ chelates as described in U.S. Pat. No. 4,965,392, the $N_3S$ chelates as described in U.S. Pat. No. 5,120,526, and the $N_2S_2$ chelates containing cleavable linkers as described in U.S. Pat. No. 5,175,257. The chelating agent is coupled to the peptide by standard methodology known in the field of the invention and may be added at any location on the peptide provided that the biological activity of the peptide is not adversely affected. Preferably, the chelating group is covalently coupled to the amino terminal amino acid of the peptide. The chelating group may advantageously be attached to the peptide during solid phase peptide synthesis or added by solution phase chemistry after the peptide has been obtained. Preferred chelating groups include DOTA, NOTA, NODAGA or CB-TE2A.

Concerning the synthesis of the peptides used in the present invention reference is made to U.S. Pat. No. 7,026,282.

The peptide/chelate conjugates of the invention are labeled by reacting the conjugate with 177-Lu radionuclide, e.g. as a metal salt, preferably water soluble. The reaction is carried out by known methods in the art.

Preferably, the radiopharmaceutical composition of the present invention is provided in a kit whereby the radionuclide is provided in one vial and the peptide/chelating group conjugate is provided in a second vial and the contents mixed just prior to administration. The mixture may be heated if necessary to effect complete labelling. The provision of such radiolabeled complexes in kit form and the preparation of the final radiolabeled product are standard and routine in the field of nuclear medicine. The final radiopharmaceutical product should be of high radiochemical purity, preferably greater than 95%, and at least greater than 90%, as determined by standard protocols known in the art.

The radiolabeled complex is prepared to provide a radioactive dose of between about 1-100 MBq in animals, preferable about 20 MBq and of 2-20 GBq in humans preferably about 7.4 GBq, to the individual in accordance with standard radiopharmaceutical dosing determinations. As used herein, "a diagnostically effective amount" means an amount of the radiopharmaceutical sufficient to permit its detection by scintigraphic means and "a therapeutically effective amount" means an amount sufficient to effect a therapeutic treatment at the targeted biological site. The radio labeled peptides may be administered intravenously in any conventional medium for intravenous injection. Imaging of the biological site may be effected within about 2-5 minutes post-injection, but may also take place several hours post-injection. Any conventional method of imaging for diagnostic purposes may be utilized.

The following example describes a preferred embodiment of the invention. Other embodiments within the scope of the claims herein will be apparent to one skilled in the art from consideration of the specification or practice of the invention as disclosed herein.

EXAMPLE

FIG. 1 shows the chemical structure and biodistribution of $^{177}$Lu-DOTA-AE105 in selected organs and primary tumor lesions in HT-29 tumor xenograft bearing Nude mice. Mice were sacrificed at 0.5, 1.0, 2.0, 4.0 and 24.0 h after injection, and a panel of organs, including blood drawn from the heart, was collected, weighed, and analyzed for radioactive content. Mean percent injected dose per gram (% ID/g)±SEM from three mice at each point is presented. A. Chemical structure of $^{177}$Lu-DOTA-AE105. B(top) Biodistribution of $^{177}$Lu-DOTA-AE105 in selected organs/tissues between 0.5 and 24.0 h. B (bottom). Shows an increased time resolution of early time poins for the biodistribution of $^{177}$Lu-DOTA-AE105 in selected organs/tissues between 0.5 and 4.0 h.

Figure 2:
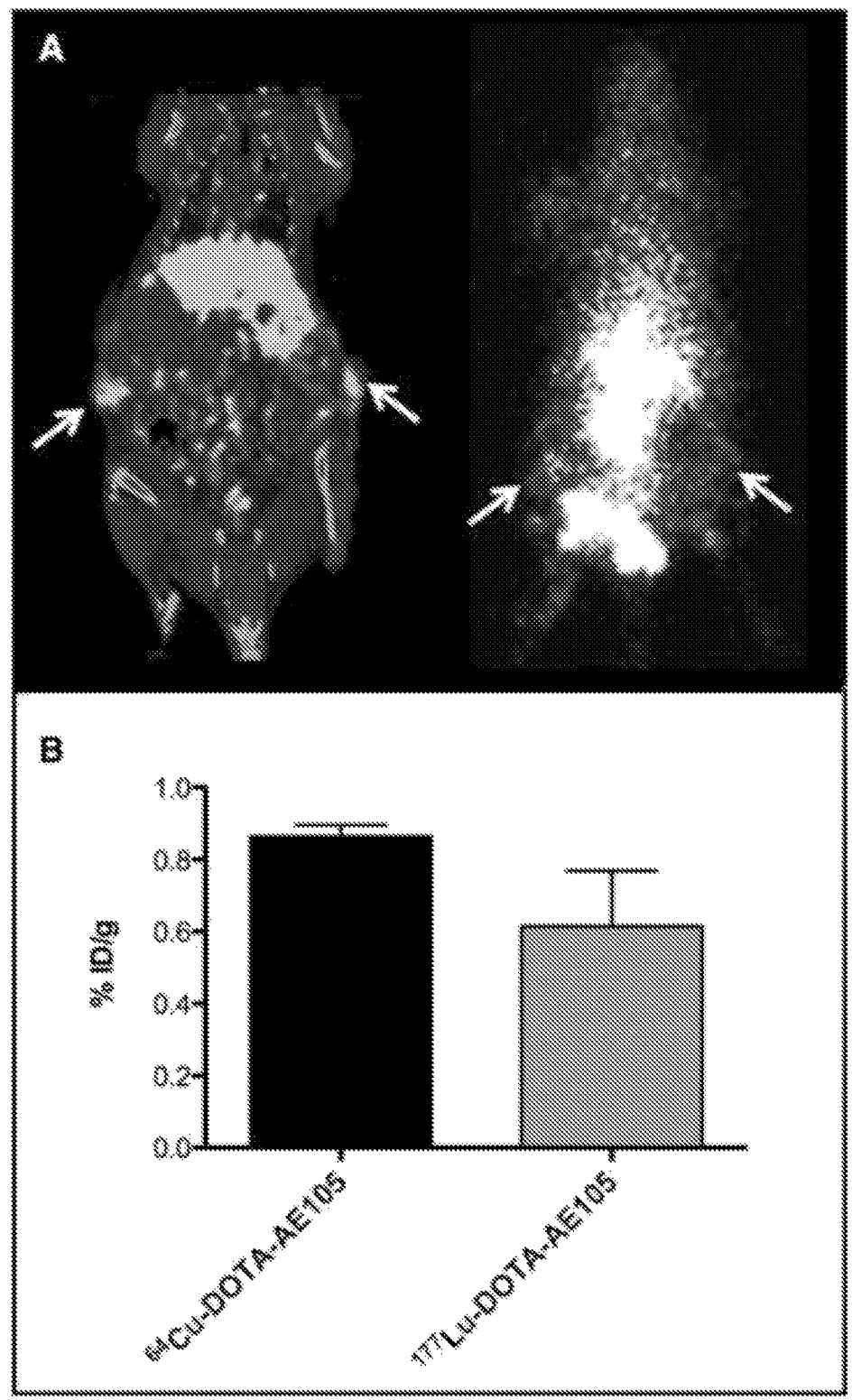
FIG. 2 shows PET/CT and gamma planar imaging of HT-29 tumor xenograft in Nude mice with quantitative tumor uptake data for comparison.

FIG. 2 shows PET/CT and gamma planar imaging of HT-29 tumor xenograft in Nude mice with quantitative tumor uptake data for comparison. For PET/CT imaging, one mouse was injected with $^{64}$Cu-DOTA-AE105 and scanned 1 h post injection. Gamma planar imaging was performed on another mouse 1 h post injection of $^{177}$Lu-DOTA-AE105. Quantitative data were based on manual drawings of region-of-interest analyses on PET/CT data and from analyzed whole tumor tissue using a gamma-counter for planar data. A. Representative images after PET/CT (left) and Gamma planar (right) imaging of HT-29 tumor xenograft. White arrows indicate tumor xenograft. B. A tumor values uptake of 0.86±0.03% ID/g and 0.61±0.15% ID/g were found for $^{64}$Cu-DOTA-AE105 (PET) and $^{177}$Lu-DOTA-AE105 (Gamma). Quantitative tumor uptake data is presented as % ID/g±SEM based on three animals.

Figure 3:
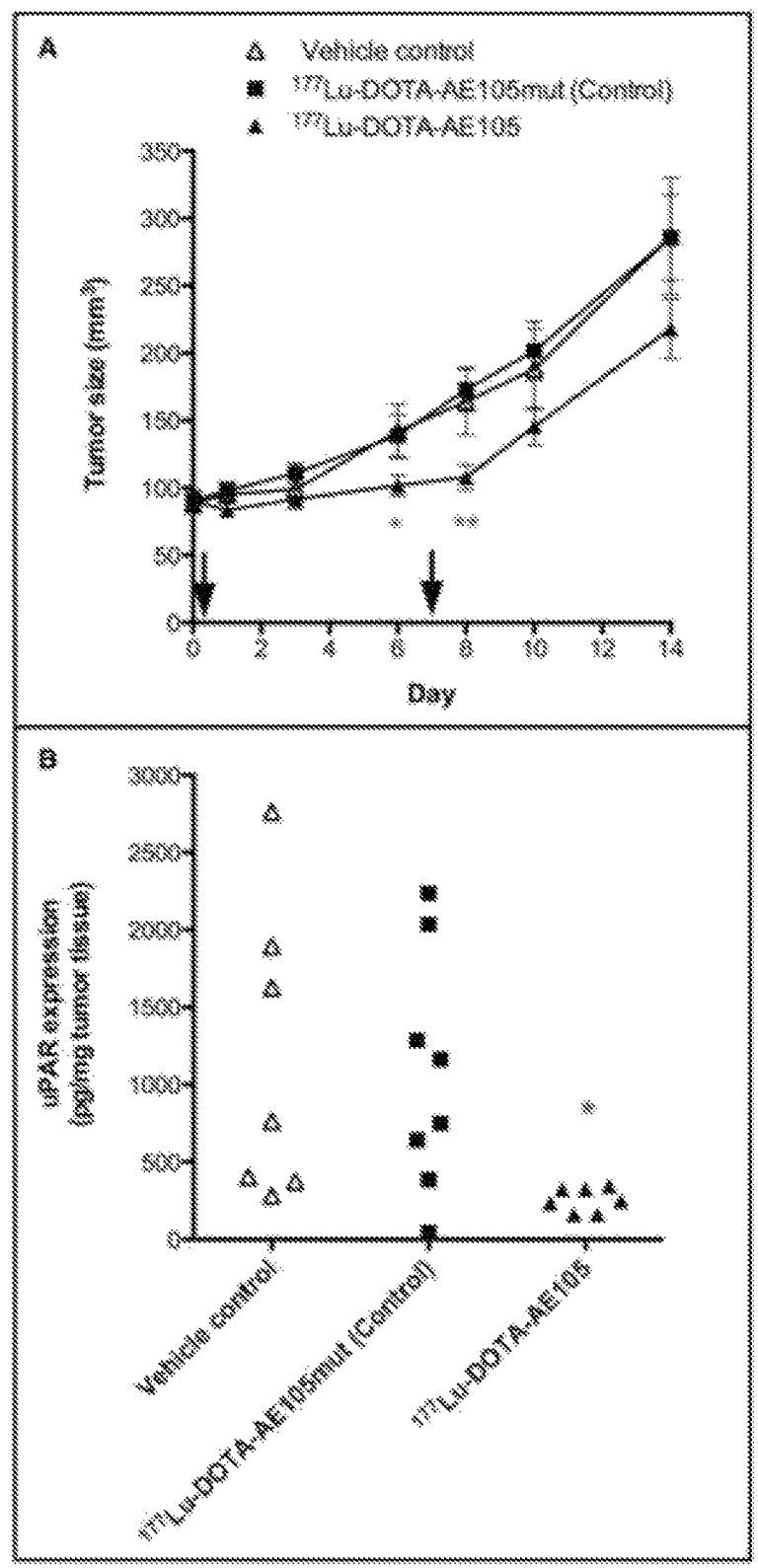
FIG. 3 shows mean tumor volume and uPAR expression levels in animals dosed with 2x20MBq of either $^{177}$Lu-DOTA-AE105, control peptide $^{177}$Lu-DOTA-AE105mut or vehicle control.

FIG. 3 shows mean tumor volume and uPAR expression levels in animals dosed with 2×20MBq of either $^{177}$Lu-DOTA-AE105, control peptide $^{177}$Lu-DOTA-AE105mut or vehicle control. A. A significant effect of $^{177}$Lu-DOTA-AE105 on tumor volume was found day 6 (p<0.05) and day 8 (p<0.01) compared with control groups. No significant differences in tumor volumes were found at end of study day 14. Mean tumor volume were calculated by manual drawing of tumor lesions on CT images. Results presented as mean±SEM, n=12 tumor/group. B. uPAR expression levels using ELISA on whole tumor extracts were determined at the end of study day 14. A significantly reduced uPAR level was found in the goups of animals dosed with $^{177}$Lu-DOTA-AE105 compared with control groups (p<0.05). No difference was found between vehicle and control peptide $^{177}$Lu-DOTA-AE105mut group.

Figure 4:
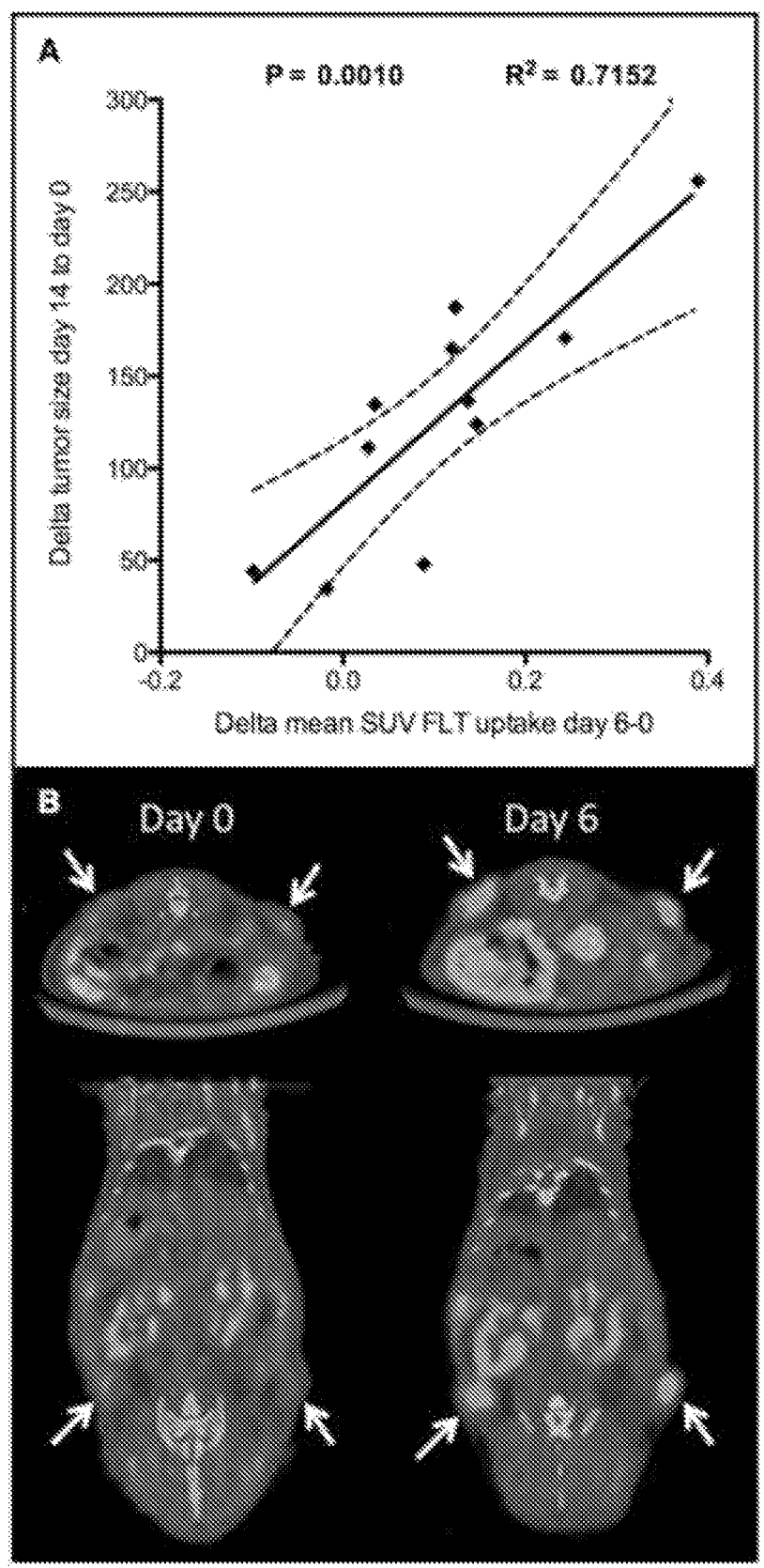
FIG. 4 shows the use of $^{18}$F-FLT PET as a predictor for efficacy of $^{177}$Lu-DOTA-AE105 treatment.

FIG. 4 shows the use of $^{18}$F-FLT PET as a predictor for efficacy of $^{177}$Lu-DOTA-AE105 treatment. All mice in the group of animals dosed with $^{177}$Lu-DOTA-AE105 were PET/CT scanned study day 0 and 6 with $^{18}$F-FLT. A. A significant correlation between the differences between mean tumor uptake of $^{18}$F-FLT day 6 vs day 0 with the difference in tumor volume day 0 to day 14, illustrating the potential of $^{18}$F-FLT PET to predict final tumor volume day 14 based on the difference in tumor uptake between day 6 and day 0. Each point represents a single tumor. B. Representative PET/CT image (axial, top), (sagital, bottom) of a Nude mouse bearing HT-29 tumor xenograft 1 h post injection of $^{18}$F-FLT day 0 (left) and day 6 (right). White arrow indicate tumor lesion.

Figure 5:
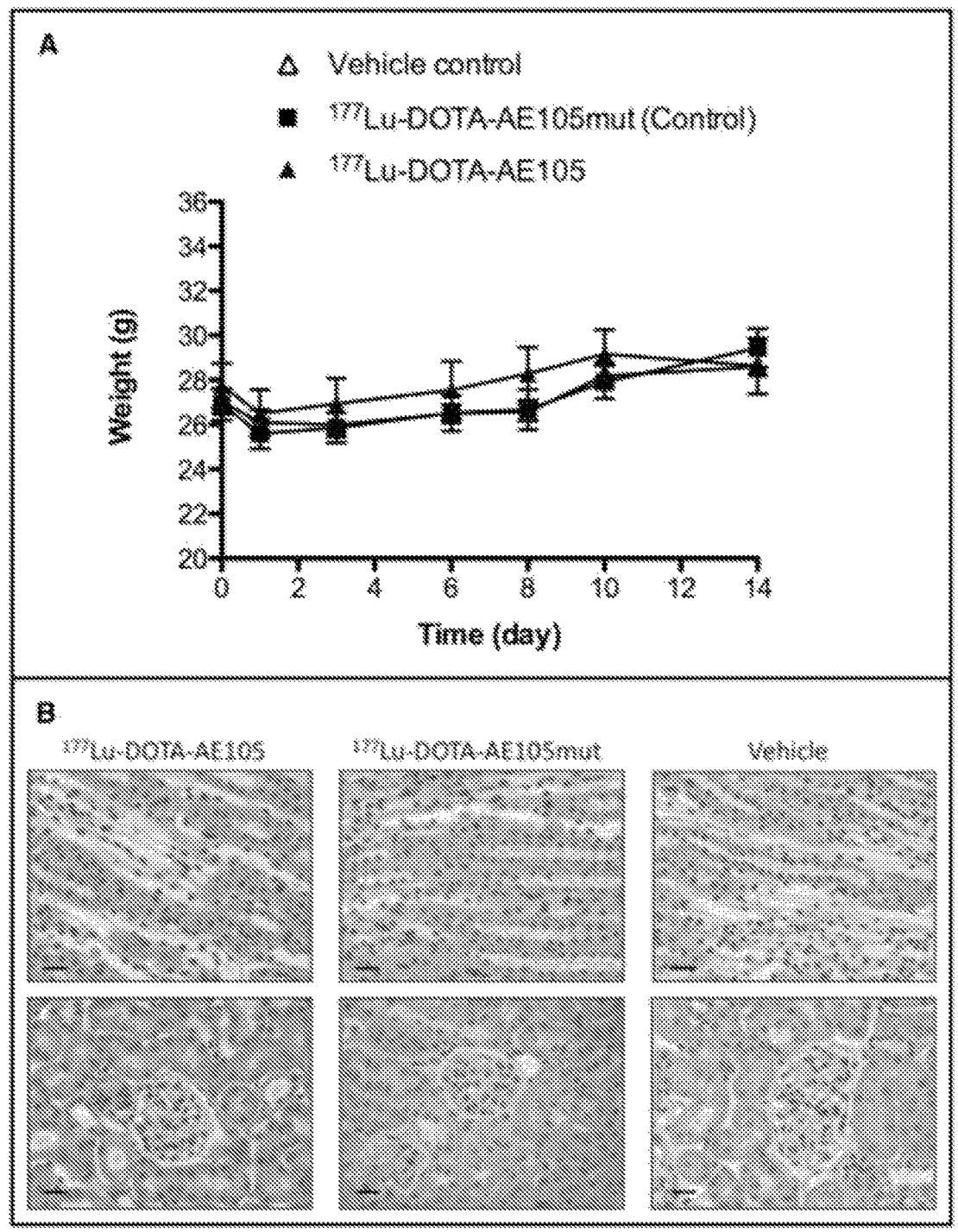
FIG. 5 shows the toxicity in animals dosed with $^{177}$Lu-DOTA-AE105, control peptide $^{177}$Lu-DOTA-AE105mut or vehicle control evaluated by following each mice weight during the study and using H&E staining on kidneys.

FIG. 5 shows the toxicity in animals dosed with $^{177}$Lu-DOTA-AE105, control peptide $^{177}$Lu-DOTA-AE105mut or vehicle control evaluated by following each mice weight during the study and using H&E staining on kidneys. A. No significant differences in the mean body weights were observed between each treatment groups. Results are presented as the mean±SEM, n=6 animals/group. B, H&E staining of kidney sections representing kidney epithelia (top) and glomerulus (Bottom) from each treatment group. A histopathological examination of the kidneys revealed no gross macroscopic morphological changes in any treatment group. One pair of kidneys from one animal/group was stained. Scale bar=25 µm, 40× zoom.

Figure 6:
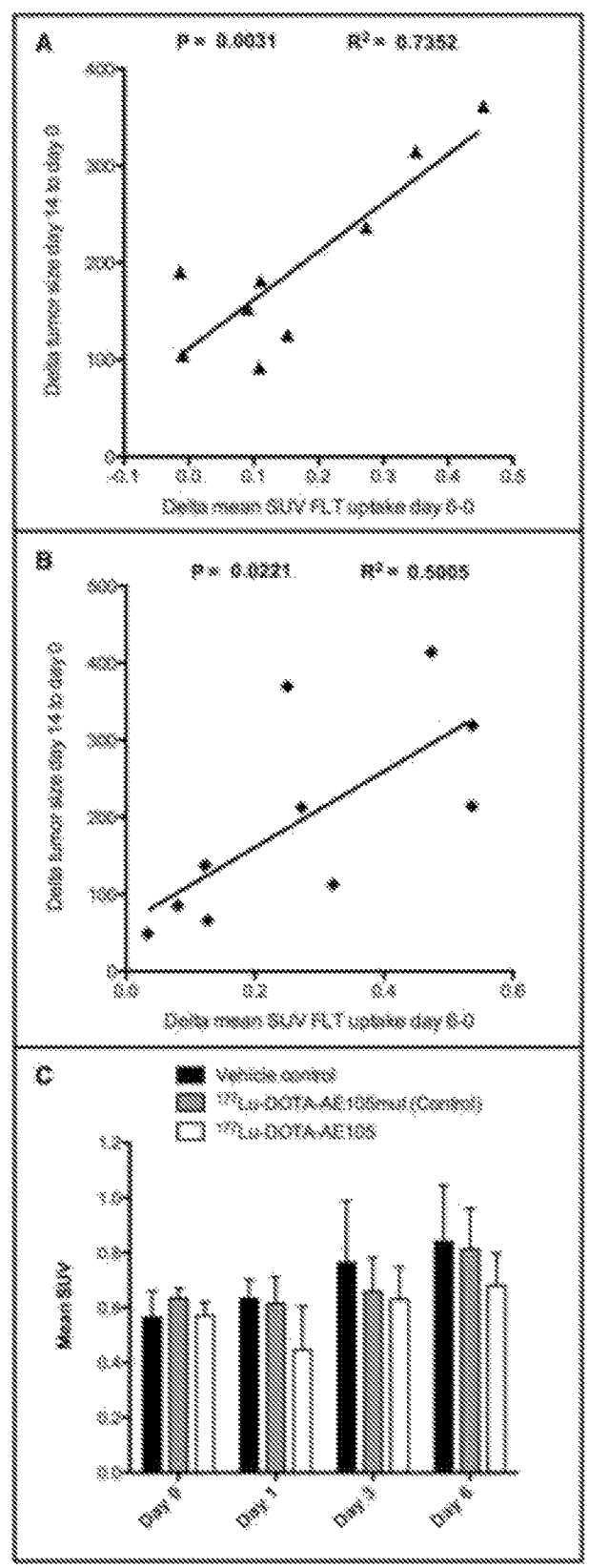
FIG. 6 shows raw data from a $^{18}$FLT-PET/CT study.

FIG. 6 shows raw data from a $^{18}$FLT-PET/CT study. A/B. Correlation between difference in tumor $^{18}$F-FLT uptake day 0 to 6 and the tumor sized day 14 in the group of mice dosed with the non-binding control peptide $^{177}$Lu-DOTA-AE105Mut (A) and vehicle (B), respectively. C. Mean groups values of tumor $^{18}$F-FLT uptake day 0, 1, 3 and 6. No significant differences between any groups were found. Results presented as mean±SEM.

Figure 7:
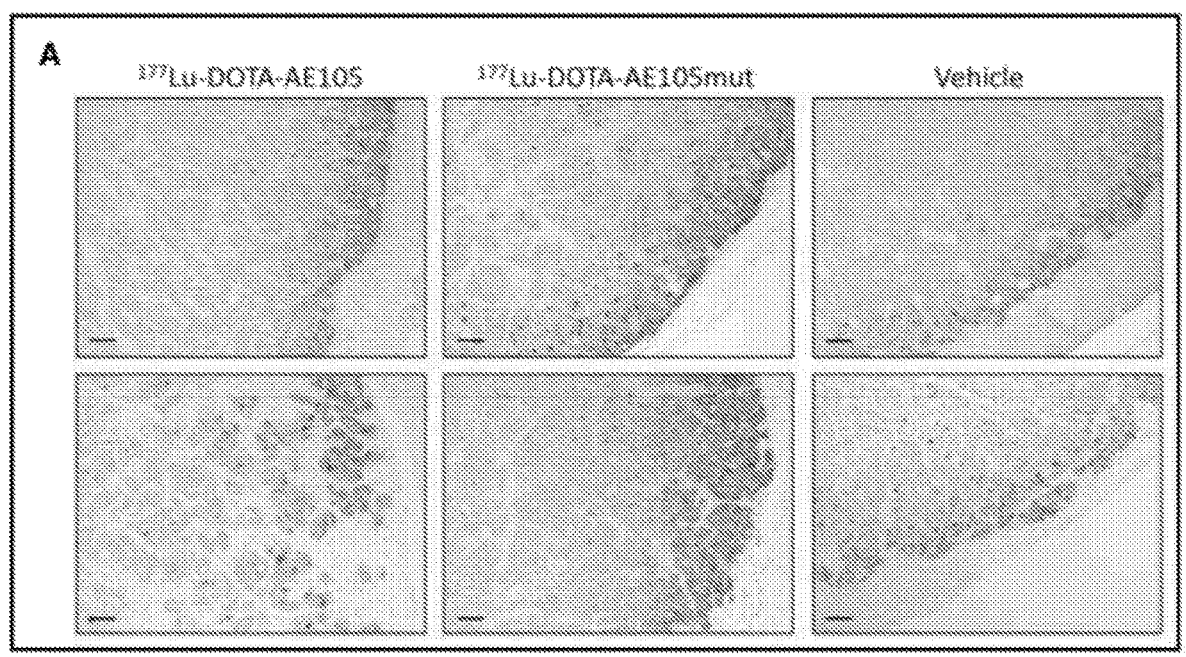
FIG. 7 shows uPAR immunohistochemical stainings in resected HT-29 tumors.

FIG. 7 shows uPAR immunohistochemical stainings in resected HT-29 tumors. Two tumors (1 mouse) from each treatment group were resected and stained for uPAR. No significant differences in staining intensity were found between the groups. All resected tumors had a primarily uPAR positive straining in the periphery of the tumor, thus confirming earlier published observations[25]. Scale bar=50 µm, 20× zoom.

Figure 8:
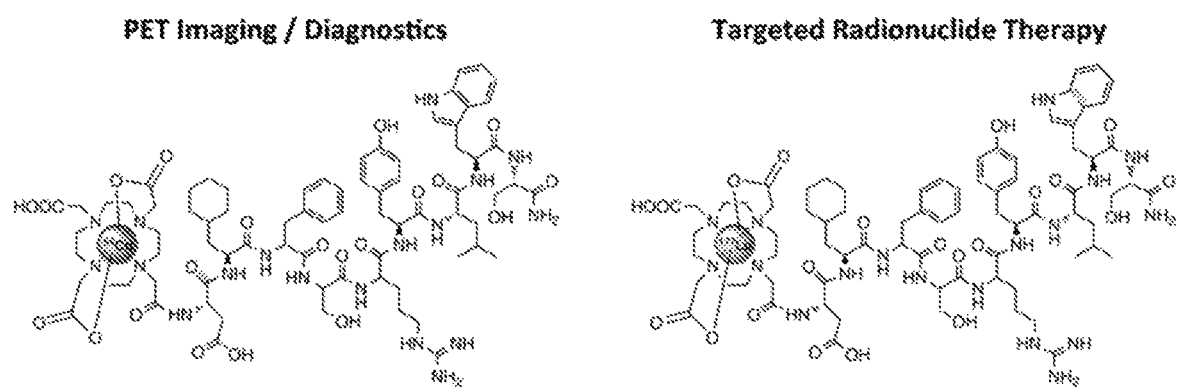
FIG. 8 shows chemical structures of a "uPAR theranostic pair" and illustration of the experimental setup in the disseminated-metastatic prostate cancer study.
Figure 8:
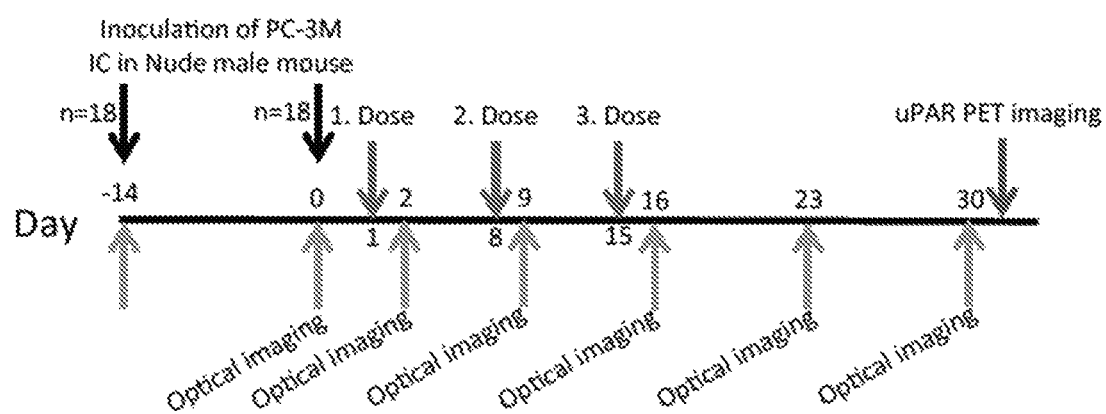

FIG. 8 shows A) Chemical structures of a "uPAR theranostic pair", $^{64}$Cu-DOTA-AE105 (PET Diagnostics) and $^{177}$Lu-DOTA-AE105 (Therapy). AE105 is a 9-mer peptide with the amino-acids sequence: Asp$^1$-Cha$^2$-Phe$^3$-ser$^4$-arg$^5$-Tyr$^6$-Leu$^7$-Trp$^8$-Ser$^9$, where residues are hot-spots for the interaction with uPAR. Cha is un-natural amino acid Cyclohexyl-(L)-alanine. ser and arg are both present in the D-configuration. B) Illustration of the experimental setup in the study. In total, 36 mice were inoculated with the uPAR positive and luciferase transfected human prostate cancer cell line PC-3M.Luc. by intra-cardiac injection 14 and 1 day before first dose. Three groups of 12 mice, 6 inoculated 14 day prior and 1 day prior to first dose where made. Each group received 3 doses one week apart with approx. 18 MBq/dose or vehicle. Tumor burden/number of metastatic lesions were monitored using bioluminescence imaging (Optical imaging) by injection of luciferin 10 min before scan. At study day 31, a uPAR PET scan using $^{64}$Cu-DOTA-AE105 was performed on 1 mouse from each treatment group, to illustrate the potential of uPAR PET to identify metastatic lesions.

Figure 9:
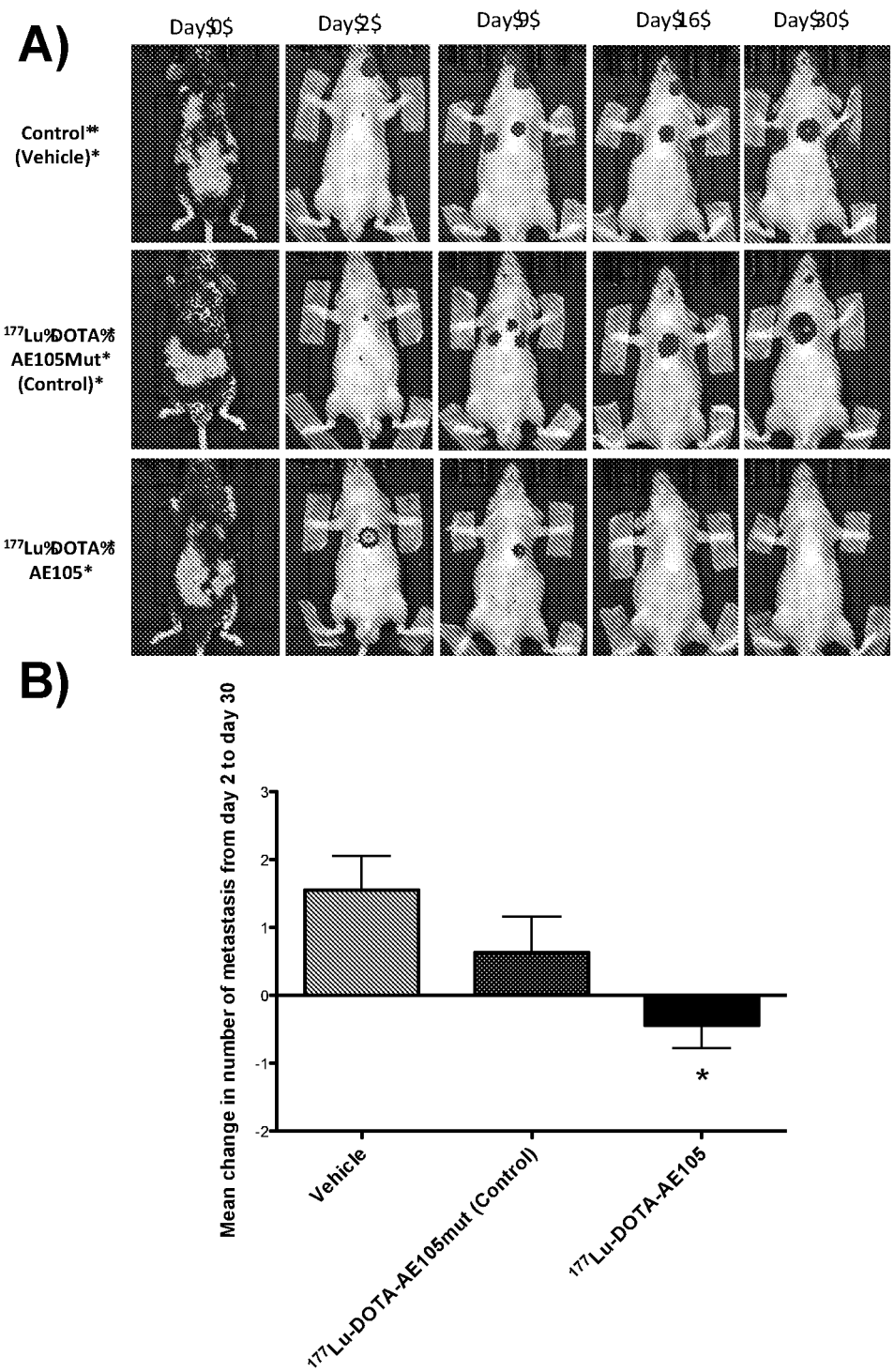
FIG. 9 shows representative bioluminescence images and quantitative analysis of the total number of metastatic lesions developed from study day 2 to 30 in the disseminated-metastatic prostate cancer study.

FIG. 9 shows A) Representative bioluminescence images for each group of treatment in the study. Increased number of metastatic lesions was observed in the two control groups, compared with the group of mice dosed with the uPAR targeted radionuclide therapy ($^{177}$Lu-DOTA-AE105). B) Quantitative analysis of the total number of metastatic lesions developed from study day 2 to 30, confirmed this observation. A significant reduction in the number of metastatic lesions was found in the 177Lu-DOTA-AE105 group, compared with the two control groups using one-way ANOVA (p=0.0193, N=12/group).

Figure 10:
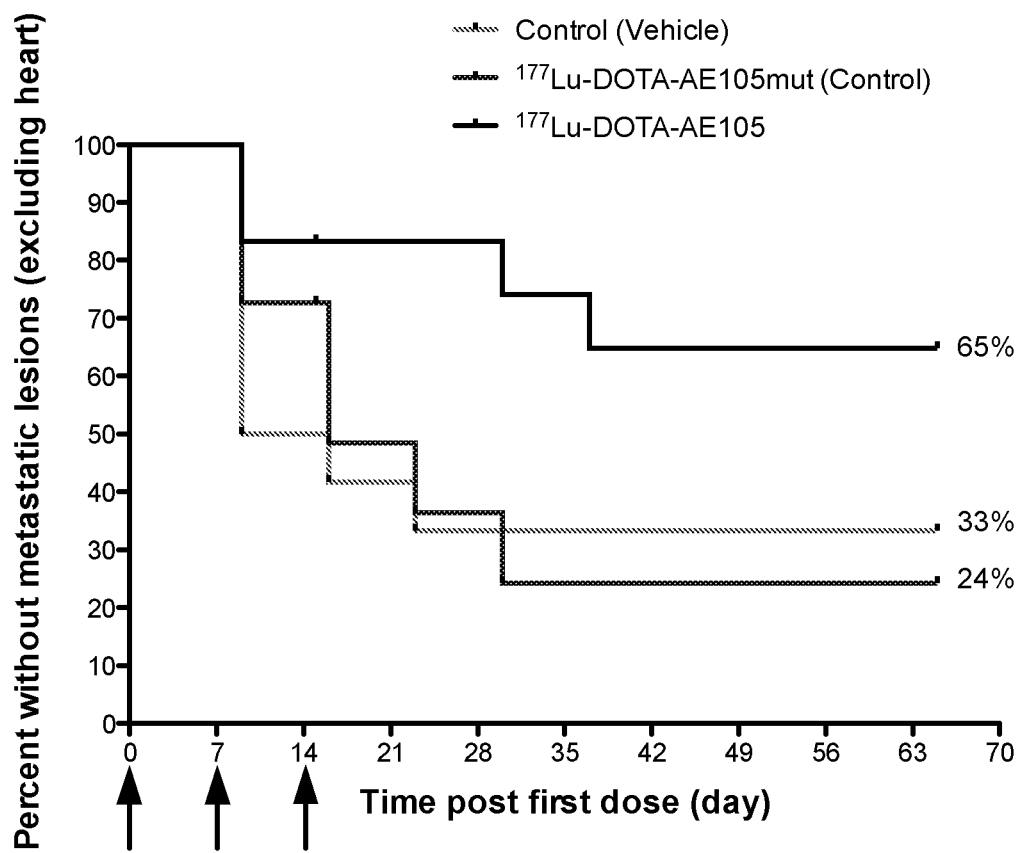
FIG. 10 shows distant metastatic-free survival in the disseminated-metastatic prostate cancer study.

FIG. 10 shows distant metastatic-free survival. A clear tendency of prolonged distant metastatic free survival was found for the uPAR-targeted treatment group ($^{177}$Lu-DOTA-AE105) by analyzing the time until first metastatic lesion (excluding heart). In 65% of the mice dosed with $^{177}$Lu-DOTA-AE105 there were no distant metastases present at day 64 post first dose. Same observation was only seen for 24% and 33% in the $^{177}$Lu-DOTA-AE105mut (control) and vehicle control group, respectively. Black arrows indicate dosing days.

Figure 11:
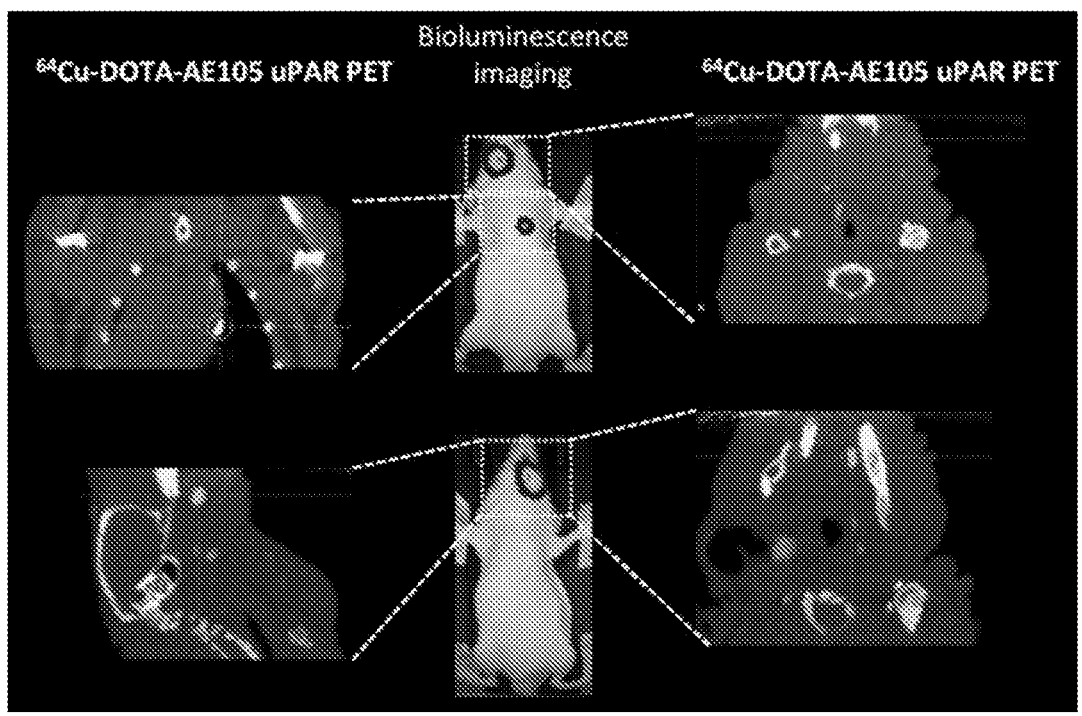
FIG. 11 shows uPAR PET imaging for identification of small metastatic lesions.

FIG. 11 shows uPAR PET imaging for identification of small metastatic lesions. uPAR PET using $^{64}$Cu-DOTA-AE105, was able to identify each tumor lesion in each mouse with high contrast and a clear correlation between uPAR PET and corresponding bioluminescence imaging was observed. This illustrates the ability for both diagnostic and therapy for this new 'uPAR theranostic pair'. uPAR PET was performed by i.v. injection of approx. 5 MBq 64Cu-DOTA-AE105 in the tail vein followed by scan 22 hr post injection.

Figure 12:
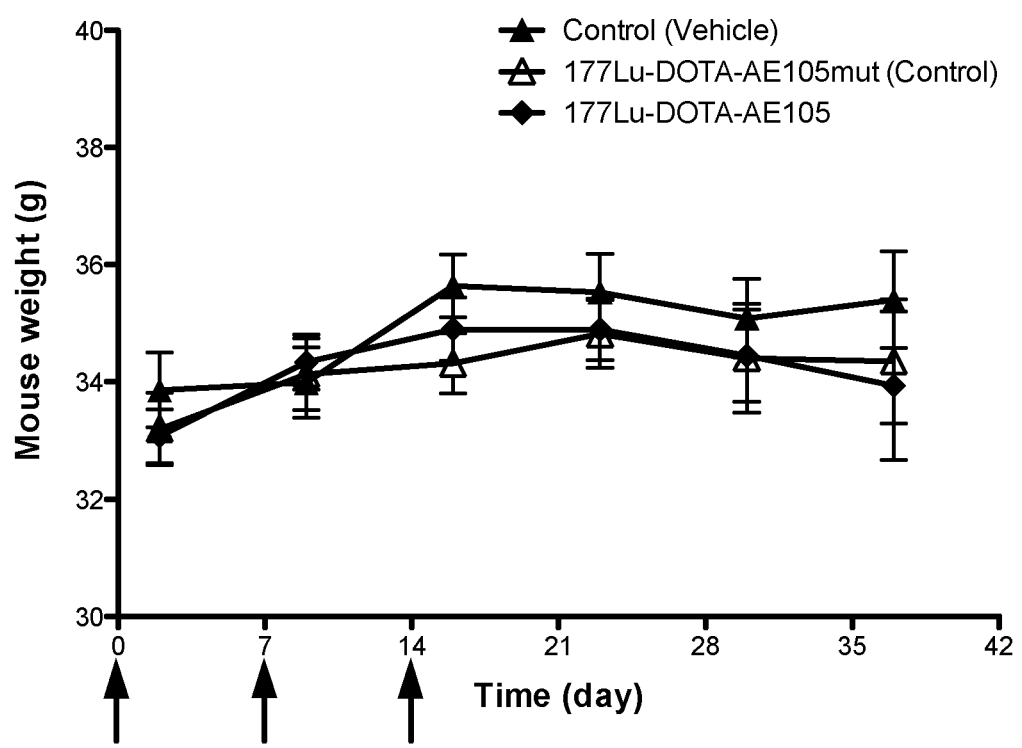
FIG. 12 shows monitoring the weight of each mouse during the in the disseminated-metastatic prostate cancer study.

FIG. 12 shows monitoring the weight of each mouse during the entire study was done to investigate for any treatment-induce toxicity. No significant difference in the mean weight of all mice in each treatment group was observed for 37 days post first injection, thus indicating that three doses of approx. 18 MBq, 1 week apart of $^{177}$Lu-DOTA-AE105 were well tolerated. Black arrows indicate dosing days.

All chemicals were purchased from Sigma-Aldrich Denmark A/S unless specified otherwise. $^{177}$Lu was purchased from PerkinElmer (Boston (Mass.), USA). All solutions were made using ultrapure water (<0.07 μSimens/cm). Reversed-phase high pressure liquid chromatography (RP-HPLC) was performed on a Waters Alliance 2795 Separations module equipped with at Waters 2489 UV/Visible detector (Waters Cooperation, Milford (Mass.), USA) and a Caroll Ramsey Assosiates 105 S-1 radioactivity detector (Berkeley, Calif., USA). RP-HPLC column was Luna C18, HST, 50×2 mm, 2.5 μm (Phenomenex, Torrance, Calif., USA). The mobile phase was 5% (v/v) acetonitrile/95% (v/v) water with 0.1% (v/v) TFA and 95% (v/v) acetonitrile/5% (v/v) water with 0.1% (v/v) TFA. TLC was performed with a Raytest MiniGita Star (Straubenhardt, Germany) TLC-scanner equipped with a Beta-detector. The TLC eluent was Ammonium acetate (0.65M) in 50% (v/v) methanol in water and the TLC-plate was a Silica60 on Al foil (Sigma-Aldrich Denmark A/S).

Recombinant human uPAR and was produced and purified as described.[29, 30]. A polyclonal rabbit anti-uPAR antibody was prepared in house using purified recombinant uPAR expressed in Chinese Hamster Ovary cells as antigen [31]. 2-(4,7,10-tris(2-tert-butoxy-2-oxoethyl)-1,4,7,10-tetraazacyclo-dodecan-1-yl)-acetic acid (DOTA-tris(tBu)ester was purchased from CheMatech (Dijon, France). $^{18}$F-FLT was obtained from productions at Department of Nuclear Medicine & PET, Copenhagen University Hospital, that is certified to produce and use this tracer in patients.

Peptide Synthesis and Radiolabeling

Two 9-mer DOTA-conjugated peptides as previously described was used[25] i.e. DOTA-AE105 (DOTA-Asp-Cha-Phe-(D)Ser-(D)Arg-Tyr-Leu-Trp-Ser-CONH$_2$) (FIG. 1A) and DOTA-AE105mut (DOTA-Asp-Cha-Glu-(D)Ser-(D)Arg-Tyr-Leu-Glu-Ser-CONH$_2$) (FIG. 1A). The radiolabeling of DOTA-AE105 with $^{64}$Cu was also done as previously reported[25]. The radiolabeling of DOTA-AE105 and DOTA-AE105mut with $^{177}$Lu was performed by adding $^{177}$LuCl$_3$ (aq solution in 0.05M HCl, 25 μl ~500 MBq) to a solution containing peptide (4.65 nmol) and sodium ascorbate (56 mg, 0.28 mmol) in 0.05M aq. HCl(450 μl). The mixture was heated to 80° C. for 60 minutes and then allowed to reach ambient temperature. The mixture was passed through a C18 SepPak cartridge and unlabeled Lu$^{3+}$ was eluded with water (5 ml). The radiolabeled peptide was finally eluted with 0.5 ml ethanol and diluted in Water for the ethanol conc. to be below 5% ready for injection. Radiochemical purity was determined by RP-HPLC and the amount of unlabeled $^{177}$LU$^{3+}$ was determined by thin layer chromatography. The synthesis typically yielded 300 MBq of radiolabeled peptide with radiochemical purities of 95-97%. The amount of unlabeled Lu$^{3+}$ was less than 1% in the final product.

Cell Lines and Animal Models

Subcutane Colorectal Cancer Xenograft Model

HT-29 colorectal cancer cells were obtained from the American Type Culture Collection (Manassas, Va., USA) and culture media was obtained from Invitrogen Co. (Carlsbad, Calif., USA). The cell line was cultured in Mc.Coy's standard medium supplemented with 10% (v/v) fetal bovine serum and 1% (v/v) penicillin/Streptomycin at 37° C. and 5% $CO_2$. Xenografts of human HT-29 colorectal cancer cells was established by injection of 200 μl cells (1×10$^8$ cells/ml) suspended in 100 μl Matrigel (BD Biosciences, San Jose, Calif., USA), subcutaneously in the left and right flank of female NMRI nude mice obtained from Taconic, under anesthesia by Hypnorm/doricum (Study day −3). All animal experiments were performed under a protocol approved by the Animal Research Committee of the Danish Ministry of Justice.

Disseminated Prostate Cancer Model

PC-3M.Luc luciferase transfected human prostate cancer cells were obtained from the American Type Culture Collection (Manassas, Va., USA) and culture media was obtained from Invitrogen Co. (Carlsbad, Calif., USA). The cell line was cultured in MEMS standard medium supplemented with 10% (v/v) fetal bovine serum and 1% (v/v) penicillin/Streptomycin at 37° C. and 5% $CO_2$.

The intra-cardiac dissemination model was established by injection of 20 μl cells (10$^5$ cells/ml) in the left ventricle in male NMRI nude mice obtained from Taconic, under anesthesia by Hypnorm/doricum (Study day −14 and −1). All animal experiments were performed under a protocol approved by the Animal Research Committee of the Danish Ministry of Justice.

Radionuclide Therapy Studies

Subcutane Colorectal Cancer Xenograft Model

Three days after tumor cell inoculation (study day 0), 18 nude mice bearing the human colorectal carcinoma xenograft HT-29 in each flank were randomly divided into three groups consisting of 6 animals each. All animals in each group were first baseline PET/CT scanned with $^{18}$F-FLT (day 0) before being dosed with 20 MBq of either $^{177}$Lu-DOTA-AE105, $^{177}$Lu-DOTA-AE105mut or vehicle. Subsequently, PET/CT scans of all mice in each group were repeated with $^{18}$F-FLT on study day 1, 3 and 6. Second treatment dose (20 MBq) was administrated on day 7, followed by CT-scan day 8, 10 and 14 to measure tumor volumes using manual ROI drawing on the reconstructed images. On day 14, all animals were euthanized and tumors and kidneys were collected and kept for further analysis at −80° C.

Disseminated Prostate Cancer Model

All mice were divided in three groups and dosed day 0, 7 and 14 with either $^{177}$Lu-DOTA-AE105 (18.3±1.1 MBq), $^{177}$Lu-DOTA-AE105mut (17.9±3.1 MBq) or vehicle by tail-vain injection during sevoflurane anesthesia. During the study period, all mice were weighted twice a week and had access to food/water ad libitum. Once a week, the number of tumor lesions were estimated using bioluminescence imaging (BLI). For BLI the mice were injected intraperitoneally with D-luciferin (150 mg/kg body weight). Images were collected using a IVIS 100 (Caliper/Xenogen). Images were acquired 10 minutes after injection of D-luciferin and the total number of lesions were calculated. A lesion was defined as flux (p s$^{-1}$) twice as high as background. Any lesions in the heart (injection site) was not included in this study, since this was not a reflection of a truly metastatic lesion.

MicroPET/CT Imaging

Ten min static PET scans were acquired with a microPET Focus 120 scanner (Siemens Medical Solutions, Malvern, Pa.) 1 hr post i.v. injection of approximately 10 MBq of either $^{64}$Cu-DOTA-AE105 or $^{18}$F-FLT during sevoflurane anesthesia. All PET/CT settings were used as described in detail previously[25]. All results were analyzed using Inveon software (Siemens Medical Solutions) and PET data was expressed as percent of injected dose per gram tissue (% ID/g), with CT-data expressed as cubic millimeters (mm$^3$).

Gamma Planar Imaging

One mouse (not enrolled in the treatment study protocol) was injected i.v. with $^{177}$Lu-DOTA-AE105 (20 MBq, 200 μL PBS) and sacrificed 1 h after injection. Static images with a gamma-camera were made with a Millenium VG with ⅝ in. NaI(TI) crystal (General Electric, Haifa, Israel). The images were acquired during 24 h in 256×256 matrix, with a zoom factor of 4.0, and the energy windows were set to 113±10% and 208±10% keV.

Biodistribution Studies

Biodistrubition study was performed as previously described[25]. In brief, Nude mice bearing HT-29 xenografts were injected in the tail-vein with 2-3 MBq of $^{177}$Lu-DOTA-AE105 or $^{177}$Lu-DOTA-AE105mut. All mice were euthanized after 0.5, 1, 2, 4 and 24 hr post tracer injection. Blood, tumor and major organs were collected (wet-weight) and the radioactivity was measured using a γ-counter from Perkin Elmer, Mass., USA (N=4 mice/group).

Dosimetry

The organ uptake values, were time integrated to obtain the residence time per gram tissue for dosimetry calculations. Integration between time 0 and 24 hr was made by the trapezoid method. All time points were used to fit to a double exponential function (2-compartment model), which was used to estimate the residence time from 24 hr to infinity. The extrapolated area was in all organs/tissues <17% of the total calculated area, except kidneys (36.1%) and spleen (30.0%). The radioactive decay of $^{177}$Lu produces mainly low energy β particles. The S value for a 1 g sphere (0.0233 mGy/MBq s) was used to calculate the organ doses by multiplying it to the organ residence values as previously described[20].

Quantification and Visualization of uPAR Expression in Resected HT-29 Tumors uPAR ELISA on resected HT-29 tumors was done as described previously in detail[25]. All results were performed as duplicate measurements. Expression of uPAR in formalin fixed and paraffin embedded tumor tissue was evaluated by immunohistochemical staining (FIG. 7) as previously published[25]. A general histopathology examination was performed on H&E stained kidney tissue (one pair of kidneys from one animal from each treatment group) and performed by a trained pathologist (ODL).

Statistical Analysis

All quantitative data are expressed as means±SEM (standard error of the mean) and means are compared using one-way ANOVA. Correlation statistics were done using linear regression analysis. P values≤0.05 were considered statistically significant.

Biodistribution and Specificity of $^{177}$Lu-DOTA-AE105

Study of the in vivo pharmacokinetics of $^{177}$Lu-DOTA-AE105 in colorectal HT-29 tumor bearing animals revealed a fast clearance rate from blood and all organs investigated after resection (FIG. 1B). Highest levels of radioactivity were found in the kidneys, tumor and blood. The levels of radioactivity in tumors peaked after 0.5 h with 1.78±0.21% ID/g and then declined rapidly to 0.17±0.02% ID/g at 4 h and 0.057±0.02% ID/g after 24 h (Table 1). The highest tumor/muscle ratio (T/M) of $^{177}$Lu-DOTA-AE105 was 12 at 1 h after injection and decreased progressively to 3.3 at 24 h after administration. A significant reduced tumor uptake (p<0.001) was observed after administration of a non-binding control peptide ($^{177}$Lu-DOTA-AE105mut) after 0.5 h compared with $^{177}$Lu-DOTA-AE105, thus confirming the specificity of the uPAR targeted peptide (Table 1).

TABLE 1

Biodistributin and dosimetri of $^{177}$Lu-DOTA-AE105 and $^{177}$Lu-DOTA-AE105mut in Nude mice bearing HT-29 tumor xenograft

| | % ID/g | | | | | | |
|---|---|---|---|---|---|---|---|
| | $^{177}$Lu-DOTA-AE105mut | $^{177}$Lu-DOTA-AE 105 | | | | | mGy/ |
| | 0.5 h | 0.5 h | 1.0 h | 2.0 h | 4.0 h | 24 h | MBq |
| Blood | 0.959 | 2.709 | 0.282 | 0.173 | 0.043 | 0.005 | 4.9 |
| Liver | 0.228 | 0.686 | 0.249 | 0.243 | 0.284 | 0.149 | 2.4 |
| Kidney | 3.013 | 6.174 | 2.440 | 1.909 | 1.667 | 0.839 | 52.9 |
| Spleen | 0.163 | 0.924 | 0.262 | 0.222 | 0.303 | 0.109 | 5.5 |
| Heart | 0.278 | 0.757 | 0.143 | 0.082 | 0.050 | 0.017 | 2.0 |
| Intestine | 0.200 | 0.579 | 0.196 | 0.271 | 0.289 | 0.078 | 2.9 |
| Muscle | 0.235 | 0.580 | 0.084 | 0.047 | 0.053 | 0.010 | 1.2 |
| Bone | 0.390 | 0.696 | 0.699 | 0.267 | 0.258 | 0.320 | 1.8 |
| Brain | 0.061 | 0.075 | 0.038 | 0.026 | 0.019 | 0.005 | 0.4 |
| Tumor | 0.708 | 1.779* | 0.614 | 0.170 | 0.176 | 0.057 | 5.8/58.0§ |

NOTE:
each data point represents a mean from three animals is expressed as procent of injected dose per gram tissue or organ
*p < 0.05
§uPAR positive tumor fraction uPAR PET and Gamma Planar Imaging Labeling DOTA-AE105 with a positron-emitting radionuclide enable the use of PET imaging for localizing uPAR positive tumors as demonstrated previously[25, 26, 28]. This is illustrated in FIG. 2A (left), where a colorectal HT-29 tumor bearing mouse was PET/CT scanned using $^{64}$Cu-DOTA-AE105. Highest uptake using this PET tracer was seen in liver and tumor tissue, thus confirming previously published data[25, 26]. In FIG. 2A (right) is a representative planar image of a HT-29 tumor bearing mice after injection of $^{177}$Lu-DOTA-AE105. Using manual ROI analysis based on fused PET/CT images, a tumor uptake of 0.86±0.03% ID/g 1 hr post injection was found for $^{64}$Cu-DOTA-AE105, with the corresponding tumor uptake of $^{177}$Lu-DOTA-AE105 was 0.61±0.15% ID/g based on gamma-counter analysis. Tumors (white arrows) were clearly visible using PET imaging, whereas the planar image had a poorer image quality.

Experimental Radionuclide Therapy of HT-29 Xenografts

A significant difference in tumor size based on consecutive CT-scans was observed for tumors (n=12) at day 6 (p=0.04) and at day 8 (p=0.002) after receiving a single dose of $^{177}$Lu-DOTA-AE105 day 0 and day 7 as compared to the control groups receiving either the non-binding version of the radiolabeled peptide ($^{177}$Lu-DOTA-AE105mut) or vehicle (Control) (FIG. 3A). No significant difference were observed at day 10 and 14. When the study was terminated at day 14, the average tumor sizes were 287±44 mm³, 286±32 mm³ and 218±22 mm³ for vehicle controls, $^{177}$Lu-DOTA-AE105mut and $^{177}$Lu-DOTA-AE105, respectively (p=0.09).

When tumors subsequently were resected and analyzed for uPAR expression on termination of the study at day 14, a significant reduced uPAR expression (p=0.02, n=10 tumors/group) was observed among mice dosed with $^{177}$Lu-DOTA-AE105 compared to the non-targeting $^{177}$Lu-DOTA-AE105mut and the vehicle group, despite the lack of significant difference in tumor size day 14 (FIG. 3B). One mouse (carrying 2 tumors) from each treatment group was chosen for organ resection to provide additional information on uPAR expression by immunohistochemistry. No observed differences in the uPAR expression levels, as found in the ELISA data (FIG. 3B), were found in these histological sections (FIG. 6), which most likely was due to the large biological variation in the uPAR expression levels observed for the 2 non-targeted groups and the choice of enrolling only a single animal from each group.

$^{18}$F-FLT PET Imaging as an Early Response Marker

The ability to use $^{18}$F-FLT PET imaging as an indicator of response to uPAR-targeted radionuclide therapy was also investigated in this therapy study. All mice were baseline $^{18}$F-FLT PET/CT scanned on day 0 before being dosed with $^{177}$Lu-DOTA-AE105, followed by $^{18}$F-FLT PET/CT scans day 1, 3 and 6. A significant correlation between the differences in tumor uptake of $^{18}$F-FLT in the group of mice receiving $^{177}$Lu-DOTA-AE105 from baseline to day 6 with the total tumor growth in the study period (14 days) was found (p=0.001, $R^2$=0.71) (FIG. 4A). Same significant correlation was found in the two control groups (FIG. 6A,B).

The ability to predict tumor size day 14 could be found as early as day 3 (p=0.02, $R^2$=0.49), whereas no such correlation was observed day 1 (data not shown). The relatively tumor uptake of $^{18}$F-FLT in the HT-29 tumor model resulted in a high tumor-to-background ratio with tumor lesions clearly visible for PET/CT analysis (FIG. 4B). No significant difference in $^{18}$F-FLT tumor uptake between each treatment group was observed in this study (FIG. 6C).

Dosimetry

Based on the biodistribution data of $^{177}$Lu-DOTA-AE105, estimates of the dosimetry were calculated (Table 1). Highest cumulative exposure of activity was found to be in the kidneys (52.9 mGy/MBq), followed by tumor tissue (5.8 mGy/MBq), spleen (5.5 mGy/MBq) and blood (4.9 mGy/MBq). However, the uPAR-positive fraction of the HT-29 tumor have previously been found only to be located in periphery of the tumor[25]. Same expression pattern was observed in this study (FIG. 7A), with uPAR-positive cancer cells only being a fraction of approximately 10% of the entire tumor. With this is mind and with the knowledge of the small penetration range of $^{177}$Lu beta radiation (<2 mm), the present inventors calculated an estimate of local uPAR-positive tumor fraction dosimetry of approximate 58 mGy/MBq, thus resulting in the highest exposure for all organs/tissue investigated.

Toxicity

No animals died prematurely in any of the groups during the study. No differences in animal weight were observed between any of the groups (FIG. 5A), thus indicating a lack of any acute toxicity after two doses (2×25 MBq) of $^{177}$Lu-DOTA-AE105. Based on the biodistribution data and dosimetry estimates, the kidneys had the highest level of accumulated activity of any normal organ and thus the highest risk of toxicity from the this treatment. However, no grossly abnormal histopathologic changes were observed in the one pair of kidneys examined from each treatment group after H&E staining (FIG. 5B).

Ligand:uPAR Interaction In Vitro and Cell Binding

The $IC_{50}$-values for the ligands were found to be 6.7 nM for both the un-conjugated peptide AE105 and the DOTA-conjugated version (DOTA-AE105) as shown in Table 2. By substituting two amino acids known to be important for the binding towards uPAR (i.e. Phe$^3$→Glu and Trp$^8$→Glu) a significant reduction in the $IC_{50}$-value was observed ($IC_{50}$>10$^3$ nM). In vitro cell binding experiments using PC-3M confirmed the ability of 177Lu-DOTA-AE105 to bind to human uPAR with high specificity. A significant higher binding was found compared with the scrambled version (177Lu-DOTA-AE105mut)(p<0.01).

Efficacy of uPAR Targeted Radiotherapy on Micrometastasis Development

PC-3M cells were inoculated by intra-cardiac injection, a well described model for disseminated metastatic disease and since the PC-3M cell line stably express luciferase, the formation of the micro-metastasis was followed with BLI in all three-treatment groups. Representative images are for each group are shown in FIG. 3A. A clear tendency of increased number of tumor lesions was observed for both vehicle- and $^{177}$Lu-DOTA-AE105mut groups, respectively. This was also confirmed by analyzing the mean change in the number of tumor lesions from day 2 to day 30 in each mouse (FIG. 9B). A significant reduction in the number of tumor lesions/mouse was observed in the group receiving $^{177}$Lu-DOTA-AE105 (−0.44±0.33), whereas an increase was observed in both $^{177}$Lu-DOTA-AE105mut (0.63±0.53) and vehicle (1.55±0.51) groups, respectively (p<0.05). Furthermore, a clear tendency of prolonged distant metastatic free survival was found for the uPAR-targeted treatment group ($^{177}$Lu-DOTA-AE105) by analyzing the time until first metastatic lesion (excluding heart) was present (FIG. 10). In 65% of the mice dosed with $^{177}$Lu-DOTA-AE105 there were no distant metastases present at day 65 post first dose. Same observation was only seen for 24% and 33% in the $^{177}$Lu-DOTA-AE105mut (control) and vehicle control group, respectively. Median metastatic-free time was 12.5, 16 and >65 days for vehicle, 177Lu-DOTA-AE105mut and 177Lu-DOTA-AE105, respectively. All major findings are presented in Table 3.

uPAR PET Imaging for Identification of Micrometastasis In Vivo

The ability of uPAR PET imaging to identify micrometastatic lesions using 64Cu-DOTA-AE105 as ligand was for the first time explored in a number of mice during the study (study day 31). Each animal was first scanned using BLI, followed by a uPAR PET scan. Number of micrometastatic lesions present using each modality was compared for each animal. All tumor lesions present using BLI was also detection using uPAR PET imaging (4/4) (FIG. 11)

Toxicolgy

No treatment-induce toxicity was observed in any of the treatment groups in this study, indicated by both the observed mouse weight curves (FIG. 12).

Discussion

In the present study, the inventors report the first proof-of-concept experimental evidence for in vivo efficacy of radionuclide therapy using a specific uPAR-targeted radionuclide ligand $^{177}$Lu-DOTA-AE105 in a human colorectal cancer model and a disseminated metastatic prostate cancer model. The present inventors found that this radionuclide therapy both has a significant effect on the growth rate of the tumor, caused a significant reduction in the number of uPAR-positive cancer cells and reduced the number of metastatic lesions. These results are highly encouraging since a substantial number of studies have identified uPAR to be strongly upregulated in the reactive tumor-stromal compartment of different cancers and to be expressed at the front of invasive cancers and related to poor prognosis. Furthermore, the results also illustrate the potential of PET imaging to localize uPAR expressing tumors and metastasis and for prediction of the subsequent treatment response after $^{177}$Lu-DOTA-AE105 using $^{18}$F-FLT-PET.

One study has previously investigated, but only in vitro, the use of a-radionuclide uPAR-targeted cytotoxity using a $^{213}$Bi-labeled and bivalent variant of the AE105 targeting peptide for disseminated ovarian cancer[32]. In that study, as mentioned the efficacy was only evaluated in vitro on cell cultures and no controls were included to evaluate whether the observed cytotoxicity actually was caused by a uPAR targeted effect. Nevertheless, they did establish the biodistribution for their lead compound, [213]Bi-P-P4D, reporting a tumor-to-kidney ratio of 0.2, 45 minutes post injection in mice bearing the intrapertoneally transplanted ovarian cancer cell line OV-MZ-6. A clear correlation between decreasing survival rate of OV-MZ-6 cells in vitro and increasing dosing of [213]Bi-P-P4D was established by colony-forming assay.

The potential impact of a future clinical application of a $^{177}$Lu-DOTA-AE105 targeted therapy in CRC would primarily be to eradicate uPAR-positive cancer cells and reactive stromal cells at the invasive front of the primary tumor. Combined with other treatment modalities, this could attenuate the metastatic dissemination of the lesion. One note of caution should nevertheless be considered as the xenotransplanted CRC animal model, which the present inventors used in the present study, is not an ideal model for the complex human CRC that clinically represents a great challenge. Although future studies evidently are required to explore the full potential of this uPAR-targeted radionuclide therapy, the present inventors have in the present model nevertheless demonstrated the effect of such a treatment modality in relatively small tumor lesions.

The dose-limiting toxicity in the clinic using peptide-receptor radionuclide therapy is generally caused by nephrotoxicity[33]. In the present case, the kidneys were also exposed to a high level of radioactivity based on dosimetry calculations (Table 1). However, a histopathological examination of H&E stained sections from each treatment group did however not disclose gross morphological differences between the three groups indicating that the radiation dose the present inventors used did not cause a severe nephrotoxicity (FIG. 5B). Moreover, in the clinic setting, the use of different kidney protection solutions such as Gelofusine and different amino acid solutions injected immediately after injection of the radiolabelled peptide, have been shown to protect the kidney from radioactivity induce damage[34]. As an indicator of general toxicity the present inventors measured the weight of all animals in each treatment group and found no significant weight difference between groups after two doses (2×25 MBq), indicating no major acute toxicity from the radiation. However, the degree of nephotoxicity after $^{177}$Lu-DOTA-AE105 dosing needs to be carefully evaluated in future human clinical trial.

In this study, the present inventors were able to find a clear correlation between changes in $^{18}$F-FLT tumor uptake between baseline and day 6 with the final tumor volume day 14. Those tumors with the highest uptake value at day 6 compared to baseline day 0, were also the tumors which had the lowest response of the treatment. The use of $^{18}$F-FLT PET to predict tumor response based on proliferation status has previously also been illustrated for both new experimental therapies in mice[35] and for different clinical approved drugs in patients[36, 37] and the study provide evidence for its use in peptide receptor radionuclide therapy. Based on the clear correlations found in this study, the new radionuclide therapy seems to induce a reduced proliferation rate, which can be attributed to both the direct beta-ionization, but also to the known bystander effect of [177]Lu[24] providing adjacent uPAR-negative cancer cells with a significant radiation, dose since only approximately 10% of all HT-29 CRC cells in the tumor are uPAR-positive[25]. This can also explain the observed significant reduction in tumor size found day 6 and day 8 in mice dose with $^{177}$Lu-DOTA-AE105 compared to the two control groups (FIG. 3A).

The ability to select future CRC patient with high tumor expression levels of uPAR and thereby also the patients with poor prognosis, using the newly established uPAR PET imaging is also highly attractive from a clinical point of view. Today, invasive procedures such as blood sampling and tumor biopsies are the only methods for establishing the level of uPAR expression in the patient. uPAR levels in the blood is only a indirect measure of the level in the tumor tissue, whereas any biopsy taken from a tumor lesion, often is not representative of the entire tumor lesion, resulting in perhaps a false low result if the area with the highest expression level is not reach. Moreover, a biopsy from a metastatic lesion is often very difficult to get and only known lesions will be investigated. Using non-invasive uPAR PET imaging could potential replace the need for biopsy procedures and give a more representative image of the uPAR expression level since the entire body is scanned, thus also resulting in the identification of any uPAR-positive metastatic lesions. Despite that $^{177}$Lu-DOTA-AE105 enable direct gamma imaging, the lack of quantification options and the reduced imaging properties due to only 9.7% being gamma radiation, further underline the utility of uPAR PET imaging for both patient selection and therapy monitoring. With the introduction of the new "theranostic" pair for uPAR, this scenario could be a realistic option for future patient managements in the clinic.

To summarize, an entire new radionuclide peptide therapy targeting uPAR has been demonstrated. A highly uPAR-specific cytotoxic effect was found in both a human colorectal xenograft cancer model and in a disseminated prostate cancer model. Based on the extensive literature establishing uPAR to be highly expressed at the invasive front of the primary tumor in cancer patients, the present inventors believe that the present inventors have developed a new theranostic modality with potential to specifically identify and target invasive cancers.

TABLE 2

Binding properties of uPAR targeting peptid

| Ligand | Amino acid sequence | $IC_{50}$ (nM) |
|---|---|---|
| AE105 | Asp$^1$-Cha$^2$-Phe$^3$-ser$^4$-arg$^5$-Tyr$^6$-Leu$^7$-Trp$^8$-Ser$^9$ | 6.7 ± 1.6 |
| DOTA-AE105 | DOTA-Asp$^1$-Cha$^2$-Phe$^3$-ser$^4$-arg$^5$-Tyr$^6$-Leu$^7$-Trp$^8$-Ser$^9$ | 6.7 ± 1.0 |
| DOTA-AE105mut | DOTA-Asp$^1$-Cha$^2$-Glu$^3$-ser$^4$-arg$^5$-Tyr$^6$-Leu$^7$-Glu$^8$-Ser$^9$ | >>10$^3$ |

Note:
Residues in bold are hot spots for the interaction with uPAR.
Cha is Cyclohexyl-(L)-alanine.
ser and arg are both present in the D-configuration.

In table 2, the amino acids sequences of each peptid conjugate with the corresponding binding affinity towards human uPAR are shown. Residues in bold is important for the interaction with uPAR. A substitution of two of these important amino acids (Phe$^3$ and Trp$^8$) with Glu, results in a complete loss of affinity towards uPAR. Illustrated by a $IC_{50}$ value above 10$^3$ nM compared with 6.7 nM for the targeted peptide conjugate (e.i. DOTA-AE105). Importantly, no reduction in affinity is caused by conjugation of DOTA chelator in the N-terminal, illustrated with identical $IC_{50}$-value between the un-conjugated peptide AE105 and the conjugated form DOTA-AE105.

TABLE 3

Summary of treatment efficiency and metastatic-free survival

|  | p-value | Control | 177Lu-DOTA-AE-105mut (Control) | 177Lu-DOTA-AE105 |
|---|---|---|---|---|
| Animals |  | n ≥ 8 | n ≥ 8 | n ≥ 8 |
| Injected activity |  | — | 3 × 18 MBq | 3 × 18 MBq |
| Treatment efficiency |  |  |  |  |
| Stable disease/response |  | 4 | 3 | 8 |
| Progression |  | 7 | 5 | 1 |
| Control vs. 177Lu-DOTA-AE105 | 0.028 |  |  |  |
| Control vs. 177Lu-DOTA-AE105mut | 0.100 |  |  |  |
| 177Lu-DOTA-AE105 vs. 177Lu-DOTA-AE105mut | 0.049 |  |  |  |
| Median metastatic-free time (days) |  | 12.5 | 16 | >65 |
| Metastatic-free day 65 |  | 33% | 24% | 65% |

In table 3, a summary of the anti-metastatic effect of $^{177}$Lu-DOTA-AE105 in a disseminated human prostate cancer mouse model is shown. A significant higher number of mice in the group doses with uPAR targeted $^{177}$Lu-DOTA-AE105 had stable disease or a response vs. progressive disease. In the control group (vehicle) 7 out of 11 had progressive disease whereas this only was found in 1 out of 9 in the $^{177}$Lu-DOTA-AE105 group (p=0.028). By comparing $^{177}$Lu-DOTA-AE105 and the non-binding control peptide conjugate $^{177}$Lu-DOTA-AE105mut, a significant difference in treatment responds was also found (p=0.049). No significant difference in treatment efficacy was observed between the two control groups (p=0.100). Furthermore, a clear tendency of prolonged distant metastatic free survival was found for the uPAR-targeted treatment group ($^{177}$Lu-DOTA-AE105) by analyzing the time until first metastatic lesion (excluding heart) was present in each mouse. In 65% of the mice dosed with $^{177}$Lu-DOTA-AE105 there were no distant metastases present at day 65 post first dose. Same observation was only seen for 24% and 33% in the $^{177}$Lu-DOTA-AE105mut (control) and vehicle control group, respectively. Median metastatic-free time was 12.5, 16 and >65 days for vehicle, $^{177}$Lu-DOTA-AE105mut and $^{177}$Lu-DOTA-AE105, respectively.

References

[1] Jemal A, Siegel R, Xu J, and Ward E. Cancer statistics, 2010. CA Cancer J Clin 2010; 60:277-300.

[2] Ferlay J, Shin H R, Bray F, Forman D, Mathers C, and Parkin D M. Estimates of worldwide burden of cancer in 2008: GLOBOCAN 2008. Int J Cancer 2010; 127:2893-917.

[3] Glazer E S, Beaty K, Abdalla E K, Vauthey J N, and Curley S A. Effectiveness of positron emission tomography for predicting chemotherapy response in colorectal cancer liver metastases. Arch Surg 2010; 145:340-5; discussion 5.

[4] Kriegbaum M P M, Haldager L, Alpizar-Alpizar W, Jacobsen B, Gårdsvoll H, Kjaer A, and Ploug M. Rational targeting of the urokinase receptor (uPAR): Development of inhibitors and non-invasive imaging probes. Current Drug Targets 2010.

[5] Mazar AP. The urokinase plasminogen activator receptor (uPAR) as a target for the diagnosis and therapy of cancer. Anticancer Drugs 2001; 12:387-400.

[6] Jacobsen B and Ploug M. The urokinase receptor and its structural homologue C4.4A in human cancer: expression, prognosis and pharmacological inhibition. Curr Med Chem 2008; 15:2559-73.

[7] Rasch M G, Lund I K, Almasi C E, and Hoyer-Hansen G. Intact and cleaved uPAR forms: diagnostic and prognostic value in cancer. Front Biosci 2008; 13:6752-62.

[8] Ganesh S, Sier C F, Griffioen G, Vloedgraven H J, de Boer A, Welvaart K, et al. Prognostic relevance of plasminogen activators and their inhibitors in colorectal cancer. Cancer Res 1994; 54:4065-71.

[9] Ganesh S, Sier C F, Heerding M M, Griffioen G, Lamers C B, and Verspaget H W. Urokinase receptor and colorectal cancer survival. Lancet 1994; 344:401-2.

[10] Ganesh S, Sier C F, Heerding M M, van Krieken J H, Griffioen G, Welvaart K, et al. Contribution of plasminogen activators and their inhibitors to the survival prognosis of patients with Dukes' stage B and C colorectal cancer. Br J Cancer 1997; 75:1793-801.

[11] Stephens R W, Nielsen H J, Christensen I J, Thorlacius-Ussing O, Sorensen S, Dano K, et al. Plasma urokinase receptor levels in patients with colorectal cancer: relationship to prognosis. J Natl Cancer Inst 1999; 91:869-74.

[12] Lomholt A F, Christensen I J, Hoyer-Hansen G, and Nielsen H J. Prognostic value of intact and cleaved forms of the urokinase plasminogen activator receptor in a retrospective study of 518 colorectal cancer patients. Acta Oncol 2010; 49:805-11.

[13] Illemann M, Bird N, Majeed A, Laerum O D, Lund L R, Dano K, et al. Two distinct expression patterns of urokinase, urokinase receptor and plasminogen activator inhibitor-1 in colon cancer liver metastases. Int J Cancer 2009; 124:1860-70.

[14] Wang Y, Liang X, Wu S, Murrell G A, and Doe W F. Inhibition of colon cancer metastasis by a 3'-end antisense urokinase receptor mRNA in a nude mouse model. Int J Cancer 2001; 92:257-62.

[15] Ahmed N, Oliva K, Wang Y, Quinn M, and Rice G. Downregulation of urokinase plasminogen activator receptor expression inhibits Erk signalling with concomitant suppression of invasiveness due to loss of uPAR-beta1 integrin complex in colon cancer cells. Br J Cancer 2003; 89:374-84.

[16] Van Buren G, 2nd, Gray M J, Dallas N A, Xia L, Lim S J, Fan F, et al. Targeting the urokinase plasminogen activator receptor with a monoclonal antibody impairs the growth of human colorectal cancer in the liver. Cancer 2009; 115:3360-8.

[17] Lee D Y and Li K C. Molecular theranostics: a primer for the imaging professional. AJR Am J Roentgenol 2011; 197:318-24.

[18] Kwekkeboom D J, de Herder W W, Kam B L, van Eijck C H, van Essen M, Kooij P P, et al. Treatment with the radiolabeled somatostatin analog [177 Lu-DOTA 0,Tyr3] octreotate: toxicity, efficacy, and survival. J Clin Oncol 2008; 26:2124-30.

[19] Jiang L, Miao Z, Kimura R H, Liu H, Cochran J R, Culter C S, et al. Preliminary evaluation of (177)Lu-labeled knottin peptides for integrin receptor-targeted radionuclide therapy. Eur J Nucl Med Mol Imaging 2011; 38:613-22.

[20] Persson M, Gedda L, Lundqvist H, Tolmachev V, Nordgren H, Malmstrom P U, et al. [177Lu]pertuzumab: experimental therapy of HER-2-expressing xenografts. Cancer Res 2007; 67:326-31.

[21] Tolmachev V, Orlova A, Pehrson R, Galli J, Baastrup B, Andersson K, et al. Radionuclide therapy of HER2-positive microxenografts using a 177Lu-labeled HER2-specific Affibody molecule. Cancer Res 2007; 67:2773-82.

[22] Wild D, Frischknecht M, Zhang H, Morgenstern A, Bruchertseifer F, Boisclair J, et al. Alpha- versus beta-particle radiopeptide therapy in a human prostate cancer model (213Bi-DOTA-PESIN and 213Bi-AMBA versus 177Lu-DOTA-PESIN). Cancer Res 2011; 71:1009-18.

[23] Blankenberg F G, Levashova Z, Goris M G, Hamby C V, Backer M V, and Backer J M. Targeted Systemic Radiotherapy with scVEGF/177Lu Leads to Sustained Disruption of the Tumor Vasculature and Intratumoral Apoptosis. J Nucl Med 2011; 52:1630-7.

[24] Akinlolu O, Ottolino-Perry K, McCart J A, and Reilly R M. Antiproliferative effects of 111In- or 177Lu-DOTA-TOC on cells exposed to low multiplicity-of-infection double-deleted vaccinia virus encoding somatostatin subtype-2 receptor. Cancer Biother Radiopharm 2010; 25:325-33.

[25] Persson M, Madsen J, Ostergaard S, Jensen M M, Jorgensen J T, Juhl K, et al. Quantitative PET of human urokinase-type plasminogen activator receptor with 64Cu-DOTA-AE105: implications for visualizing cancer invasion. J Nucl Med 2012; 53:138-45.

[26] Li Z B, Niu G, Wang H, He L, Yang L, Ploug M, et al. Imaging of urokinase-type plasminogen activator receptor expression using a 64Cu-labeled linear peptide antagonist by microPET. Clin Cancer Res 2008; 14:4758-66.

[27] Ploug M, Ostergaard S, Gardsvoll H, Kovalski K, Hoist-Hansen C, Holm A, et al. Peptide-derived antagonists of the urokinase receptor. affinity maturation by combinatorial chemistry, identification of functional epitopes, and inhibitory effect on cancer cell intravasation. Biochemistry 2001; 40:12157-68.

[28] Persson M, Madsen J, Ostergaard S, Ploug M, and Kjaer A. (68)Ga-labeling and in vivo evaluation of a uPAR binding DOTA- and NODAGA-conjugated peptide for PET imaging of invasive cancers. Nucl Med Biol 2011.

[29] Jacobsen B, Gardsvoll H, Juhl Funch G, Ostergaard S, Barkholt V, and Ploug M. One-step affinity purification of recombinant urokinase-type plasminogen activator receptor using a synthetic peptide developed by combinatorial chemistry. Protein Expr Purif 2007; 52:286-96.

[30] Lin L, Gardsvoll H, Huai Q, Huang M, and Ploug M. Structure-based engineering of species selectivity in the interaction between urokinase and its receptor: implication for preclinical cancer therapy. J Biol Chem 2010; 285:10982-92.

[31] Ronne E, Hoyer-Hansen G, Brunner N, Pedersen H, Rank F, Osborne C K, et al. Urokinase receptor in breast cancer tissue extracts. Enzyme-linked immunosorbent assay with a combination of mono- and polyclonal antibodies. Breast Cancer Res Treat 1995; 33:199-207.

[32] Qu C F, Song E Y, Li Y, Rizvi S M, Raja C, Smith R, et al. Pre-clinical study of 213Bi labeled PAI2 for the control of micrometastatic pancreatic cancer. Clin Exp Metastasis 2005; 22:575-86.

[33] Gotthardt M, van Eerd-Vismale J, Oyen W J, de Jong M, Zhang H, Rolleman E, et al. Indication for different mechanisms of kidney uptake of radiolabeled peptides. J Nucl Med 2007; 48:596-601.

[34] Rolleman E J, Melis M, Valkema R, Boerman O C, Krenning E P, and de Jong M. Kidney protection during peptide receptor radionuclide therapy with somatostatin analogues. Eur J Nucl Med Mol Imaging 2010; 37:1018-31.

[35] Jensen M M, Erichsen K D, Bjorkling F, Madsen J, Jensen P B, Hojgaard L, et al. Early detection of response to experimental chemotherapeutic Top216 with [18F]FLT and [18F]FDG PET in human ovary cancer xenografts in mice. PLoS One 2010; 5:e12965.

[36] Herrmann K, Buck A K, Schuster T, Junger A, Wieder H A, Graf N, et al. Predictive value of initial 18F-FLT uptake in patients with aggressive non-Hodgkin lymphoma receiving R-CHOP treatment. J Nucl Med 2011; 52:690-6.

[37] Zander T, Scheffler M, Nogova L, Kobe C, Engel-Riedel W, Hellmich M, et al. Early prediction of nonprogression in advanced non-small-cell lung cancer treated with erlotinib by using [(18)F]fluorodeoxyglucose and [(18)F] fluorothymidine positron emission tomography. J Clin Oncol 2011; 29:1701-8.

The invention claimed is:

1. A 177-Lu labelled uPAR binding peptide conjugate having the formula

2. A 177-Lu labelled peptide conjugate, wherein the peptide is coupled to 177-Lu by a chelating agent and wherein the peptide is selected from the group consisting of:
(D-Asp)-([beta]-cyclohexyl-L-alanine)-(Phe)-(D-Ser)-(D-Arg)-(Tyr)-(Leu)-(Trp)-(Ser);
(Ser)-(Leu)-([beta]-cyclohexyl-L-alanine)-(Phe)-(D-Ser)-(Gln)-(Tyr)(Leu)-(Trp)-(Ser);
(D-Glu)-([beta]-cyclohexyl-L-alanine)-(Phe)-(D-Ser)-(D-Tyr)-(Tyr)-(Leu)-(Trp)-(Ser);
(Asp)-([beta]-cyclohexyl-L-alanine)-(Phe)-(D-Ser)-(D-Arg)-(Tyr)-(Leu)-(Trp)-(Ser);
(Asp)-([beta]-cyclohexyl-L-alanine)-(Phe)-(Ser)-(D-Arg)-(Tyr)-Leu)-(Trp)-(Ser);
(D-Asp)-([beta]-cyclohexyl-L-alanine)-(Phe)-(Ser)-(D-Arg)-(Tyr)-Leu)-(Trp)-(Ser);
(D-Thr)-([beta]-cyclohexyl-L-alanine)-(Phe)-(D-Ser)-(D-Arg)-(Tyr)-(Leu)-(Trp)-(Ser);
(D-Asp)-([beta]-cyclohexyl-L-alanine)-(Phe)-(D-Ser)-(D-Arg)-(Tyr)-(Leu)-([beta]-2-naphthyl-L-alanine)-(Ser);
(Asp)-([beta]-cyclohexyl-L-alanine)-(Phe)-(D-Ser)-(Arg)-(Tyr)-(Leu)-(Trp)-(Ser), (Asp)-([beta]-cyclohexyl-L-alanine)-(Phe)-(D-Ser)-(D-Arg)-(Tyr)-(Leu)([beta]-1-naphthyl-L-alanine)-(Ser);
(D-Glu)-([beta]-cyclohexyl-L-alanine)-(Phe)-(D-Ser)-(Tyr)-(Tyr)-(Leu)-(Trp)-(Ser);
(Asp)-([beta]-cyclohexyl-L-alanine)-(Phe)-(D-Ser)-(D-Arg)-(Leu)-(Leu)-(Trp)-(D-His);
(Asp)-([beta]-cyclohexyl-L-alanine)-(Phe)-(D-Ser)-(D-Arg)-([beta]-cyclohexyl-L-alanine)-(Leu)-(Trp)-(Ile);
(Asp)-([beta]-cyclohexyl-L-alanine)-(Phe)-(D-Ser)-(D-Arg)-(Tyr)-(Leu)([beta]-1-naphthyl-L-alanine)-(D-His);
(Asp)-([beta]-cyclohexyl-L-alanine)-(Phe)-(D-Ser)-(D-Arg)-(N-(2,3-dimethoxybenzyl)glycine)-(D-Phe)-(N-(3-indolylethyl)glycine)-(N-(2-methoxyethyl)glycine);
(Asp)-([beta]-cyclohexyl-L-alanine)-(Phe)-(D-Ser)-(D-Arg)-(N-(2,3-dimethoxybenzyl)glycine)-(D-Phe)-(N-benzylglycine)-(N-(2 [beta]thoxyethyl)glycine); and
(Asp)-([beta]-cyclohexyl-L-alanine)-(Phe)-(D-Ser)-(D-Arg)-(N-(2,3-dimethoxybenzyl)glycine)-(D-Phe)-(N-(2,3-dimethoxybenzyl)glycine)-(Ile).

3. The 177-Lu labelled peptide conjugate of claim 2, wherein the chelating agent is DOTA, NOTA, NODAGA or CB-TE2A.

4. The 177-Lu labelled peptide conjugate of claim 2, wherein the peptide is (D-Asp)-([beta]-cyclohexyl-L-alanine)-(Phe)-(D-Ser)-(D-Arg)-(Tyr)-(Leu)-(Trp)-(Ser).

5. A method of treatment of a cancer disease associated with high uPAR expression by administering to a patient a 177-Lu labelled peptide conjugate having the formula

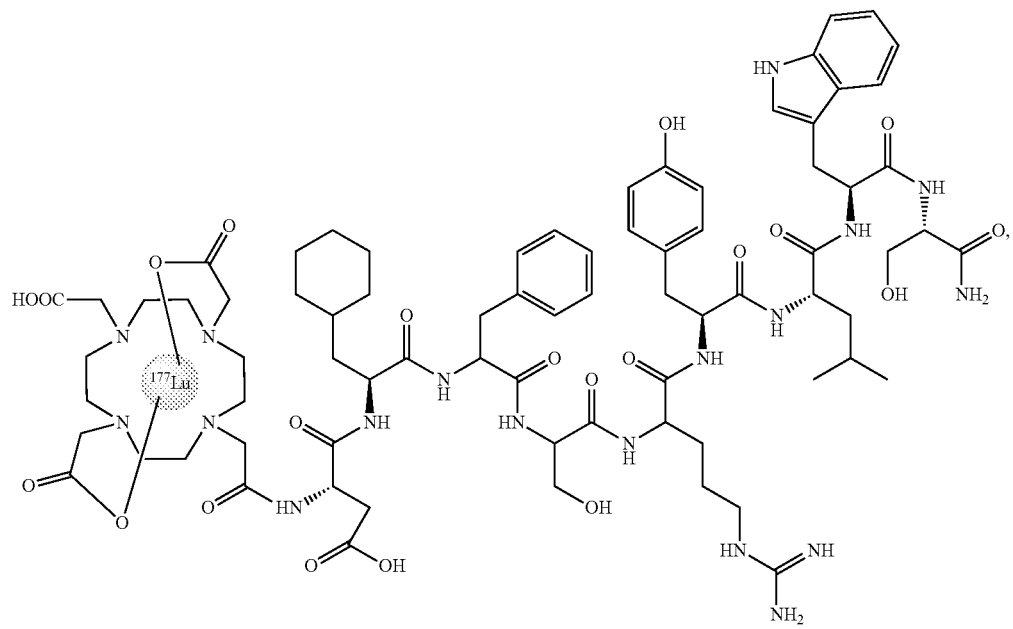

wherein the cancer disease associated with high uPAR expression is selected from colorectal cancer and prostate cancer.

6. A method of treatment of a cancer disease associated with high uPAR expression by administering to a patient the 177-Lu labeled peptide conjugate of claim 2, wherein the cancer disease associated with high uPAR expression is selected from colorectal cancer and prostate cancer.

* * * * *

UNITED STATES PATENT AND TRADEMARK OFFICE
CERTIFICATE OF CORRECTION

PATENT NO. : 10,994,032 B2  
APPLICATION NO. : 14/399820  
DATED : May 4, 2021  
INVENTOR(S) : Andreas Kjaer, Morten Persson and Michael Ploug Page 1 of 1

It is certified that error appears in the above-identified patent and that said Letters Patent is hereby corrected as shown below:

In the Claims

At Column 20, Lines 30-65, delete the formula in its entirety and insert the below formula:

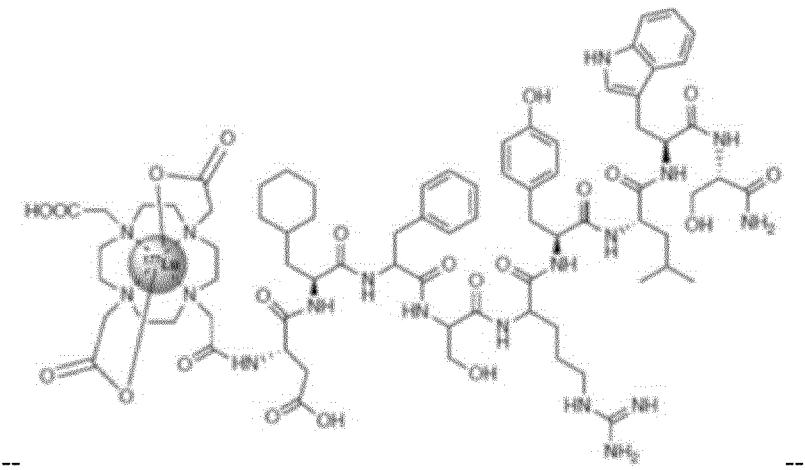

--                                                  --

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*